(12) United States Patent
McManus et al.

(10) Patent No.: US 8,916,693 B2
(45) Date of Patent: Dec. 23, 2014

(54) MONOCONJUGATED CHITOSANS AS DELIVERY AGENTS FOR SMALL INTERFERING NUCLEIC ACIDS

(75) Inventors: Samuel P. McManus, Huntsville, AL (US); Antoni Kozlowski, Huntsville, AL (US); Patrick D. Youso, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 161 days.

(21) Appl. No.: 13/496,170

(22) PCT Filed: Sep. 16, 2010

(86) PCT No.: PCT/US2010/049179
§ 371 (c)(1),
(2), (4) Date: May 23, 2012

(87) PCT Pub. No.: WO2011/035065
PCT Pub. Date: Mar. 24, 2011

(65) Prior Publication Data
US 2012/0238735 A1    Sep. 20, 2012

Related U.S. Application Data

(60) Provisional application No. 61/243,516, filed on Sep. 17, 2009.

(51) Int. Cl.
*C08B 37/08* (2006.01)
*C07H 21/02* (2006.01)
*A61K 47/48* (2006.01)

(52) U.S. Cl.
CPC ..... *A61K 47/48092* (2013.01); *A61K 47/48215* (2013.01)
USPC .......................................................... 536/20

(58) Field of Classification Search
None
See application file for complete search history.

(56) References Cited

U.S. PATENT DOCUMENTS

| | | | |
|---|---|---|---|
| 4,810,646 A | 3/1989 | Jamas et al. | |
| 4,992,540 A | 2/1991 | Jamas et al. | |
| 5,028,703 A | 7/1991 | Jamas et al. | |
| 5,607,677 A | 3/1997 | Jamas et al. | |
| 5,672,662 A | 9/1997 | Harris et al. | |
| 5,741,495 A | 4/1998 | Jamas et al. | |
| 5,898,031 A | 4/1999 | Crooke | |
| 5,932,462 A | 8/1999 | Harris et al. | |
| 6,107,094 A | 8/2000 | Crooke | |
| 6,433,040 B1 | 8/2002 | Dellamary et al. | |
| 6,565,885 B1 | 5/2003 | Tarara et al. | |
| 6,946,117 B1 | 9/2005 | Schutt et al. | |
| 7,056,704 B2 | 6/2006 | Tuschl et al. | |
| 7,078,196 B2 | 7/2006 | Tuschl et al. | |
| 7,223,803 B2 | 5/2007 | Harris et al. | |
| 2002/0086356 A1 | 7/2002 | Tuschl et al. | |
| 2003/0108923 A1 | 6/2003 | Tuschl et al. | |
| 2003/0190654 A1 | 10/2003 | Heidenreich et al. | |
| 2003/0206887 A1 | 11/2003 | Morrissey et al. | |
| 2004/0001811 A1 | 1/2004 | Kreutzer et al. | |
| 2004/0038921 A1 | 2/2004 | Kreutzer et al. | |
| 2004/0053875 A1 | 3/2004 | Kreutzer et al. | |
| 2004/0072779 A1 | 4/2004 | Kreutzer et al. | |
| 2004/0091457 A1 | 5/2004 | John et al. | |
| 2004/0102408 A1 | 5/2004 | Kreutzer et al. | |
| 2004/0121348 A1 | 6/2004 | Kreutzer et al. | |
| 2004/0126791 A1 | 7/2004 | Wajant et al. | |
| 2004/0175703 A1 | 9/2004 | Kreutzer et al. | |
| 2004/0180351 A1 | 9/2004 | Giese et al. | |
| 2004/0259247 A1 | 12/2004 | Tuschl et al. | |
| 2004/0259248 A1 | 12/2004 | Tuschl et al. | |
| 2005/0026278 A1 | 2/2005 | Tuschl et al. | |
| 2005/0043263 A1 | 2/2005 | Giese et al. | |
| 2005/0059005 A1 | 3/2005 | Tuschl et al. | |
| 2005/0074757 A1 | 4/2005 | Kreutzer et al. | |
| 2005/0100907 A1 | 5/2005 | Kreutzer et al. | |
| 2005/0176667 A1 | 8/2005 | Vornlocher | |
| 2005/0182005 A1 | 8/2005 | Tuschl et al. | |
| 2005/0186591 A1 | 8/2005 | Bumcrot et al. | |
| 2005/0227934 A1 | 10/2005 | Stoffel et al. | |
| 2005/0234006 A1 | 10/2005 | Tuschl et al. | |
| 2005/0234007 A1 | 10/2005 | Tuschl et al. | |
| 2005/0244858 A1 | 11/2005 | Rossi et al. | |
| 2005/0277610 A1 | 12/2005 | Rossi et al. | |
| 2005/0281781 A1 | 12/2005 | Ostroff | |
| 2005/0288244 A1 | 12/2005 | Manoharan et al. | |
| 2006/0008822 A1 | 1/2006 | Manoharan et al. | |
| 2006/0014289 A1 | 1/2006 | Ahmadian et al. | |

(Continued)

FOREIGN PATENT DOCUMENTS

| | | |
|---|---|---|
| EP | 1 144 623 | 8/2002 |
| EP | 1 214 945 | 6/2005 |

(Continued)

OTHER PUBLICATIONS

Olteanu, Scientific Study & Research, vol. VIII (3), 2007.*
Amarzguioui, et al., "Rational design and in vitro and in vivo delivery of Dicer substrate siRNA", Nature Protocols, vol. 1, No. 2, pp. 508-517, (2006).
Chan, et al., "Synthesis and characterization of chitosan-g-poly(ethylene glycol)-folate as a non-viral carrier for tumor-targeted gene delivery", Biomaterials, vol. 28, pp. 540-549, (2007).
De Fougerolles, et al., "Interfering with disease: a progress report on siRNA-based therapeutics", Nature Reviews, vol. 6, pp. 443-453, (Jun. 2007).
Duan, et al., "Cationic nano-copolymers mediated *IKKβ* targeting siRNA inhibit the proliferation of human Tenon's capsule fibroblasts in vitro", Molecular Vision, vol. 14, pp. 2616-2628, (2008).
Hatanaka, et al., "One-Step Synthesis of Biotinyl Photoprobes from Unprotected Carbohydrates", J. Org. Chem., vol. 65, pp. 5639-5643, (2000).

(Continued)

*Primary Examiner* — Layla Bland
(74) *Attorney, Agent, or Firm* — Mark A. Wilson

(57) ABSTRACT

Conjugates are provided, an exemplary conjugating having a single water-soluble, non-peptidic polymer, such as a poly (ethylene oxide), attached to a chitosan. Complexes of small interfering nucleic acids formed with such conjugates as well as small interfering nucleic acids attached to such conjugates are also provided. Related methods, intermediates, and compositions are also provided.

2 Claims, No Drawings

(56) References Cited

U.S. PATENT DOCUMENTS

| | | |
|---|---|---|
| 2006/0035254 A1 | 2/2006 | Manoharan et al. |
| 2006/0035815 A1 | 2/2006 | Chen et al. |
| 2006/0122137 A1 | 6/2006 | Quay et al. |
| 2006/0142230 A1 | 6/2006 | Quay |
| 2006/0160123 A1 | 7/2006 | Quay |
| 2006/0166910 A1 | 7/2006 | Tuschl et al. |
| 2006/0212950 A1 | 9/2006 | Tuschl et al. |
| 2006/0287260 A1 | 12/2006 | Manoharan et al. |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0054279 A1 | 3/2007 | Manoharan et al. |
| 2007/0093445 A1 | 4/2007 | Tuschl et al. |
| 2007/0155658 A1 | 7/2007 | Quay et al. |
| 2007/0160980 A1 | 7/2007 | Haeberli et al. |
| 2007/0161595 A1 | 7/2007 | Bumcrot et al. |
| 2007/0172430 A1 | 7/2007 | Brito et al. |
| 2007/0185050 A1 | 8/2007 | Heidenreich et al. |
| 2007/0197460 A1 | 8/2007 | Fougerolles et al. |
| 2007/0213257 A1 | 9/2007 | Sweedler |
| 2007/0213292 A1 | 9/2007 | Stoffel et al. |
| 2007/0213293 A1 | 9/2007 | McSwiggen et al. |
| 2007/0229266 A1 | 10/2007 | Gibson |
| 2007/0254362 A1 | 11/2007 | Quay et al. |
| 2007/0265220 A1 | 11/2007 | Rossi et al. |
| 2007/0269892 A1 | 11/2007 | Adami et al. |
| 2007/0275465 A1 | 11/2007 | Woppmann et al. |
| 2007/0275923 A1 | 11/2007 | Chen et al. |
| 2007/0276134 A1 | 11/2007 | Sweedler et al. |
| 2007/0281900 A1 | 12/2007 | Cui et al. |
| 2007/0287179 A1 | 12/2007 | Tuschl et al. |
| 2007/0293449 A1 | 12/2007 | Cui et al. |
| 2007/0293657 A1 | 12/2007 | Adami et al. |
| 2008/0044438 A1 | 2/2008 | Ostroff et al. |
| 2008/0070856 A1 | 3/2008 | Kreutzer et al. |
| 2008/0076701 A1 | 3/2008 | Quay et al. |
| 2008/0194512 A1 | 8/2008 | John et al. |
| 2011/0213013 A1 | 9/2011 | McManus et al. |
| 2012/0100096 A1 | 4/2012 | McManus et al. |

FOREIGN PATENT DOCUMENTS

| | | |
|---|---|---|
| EP | 1 352 061 | 5/2006 |
| EP | 1 527 176 | 1/2007 |
| EP | 1 857 547 | 11/2007 |
| EP | 1 536 827 | 1/2009 |
| EP | 1 551 868 | 1/2009 |
| EP | 2070950 A1 * | 6/2009 |
| WO | WO 2004/035615 | 4/2004 |
| WO | WO 2005/000320 | 1/2005 |
| WO | WO 2005/105152 | 11/2005 |
| WO | WO 2006/023544 | 3/2006 |
| WO | WO 2006/069782 | 7/2006 |
| WO | WO 2007/084684 | 7/2007 |
| WO | WO 2007/121947 | 11/2007 |
| WO | WO 2007/121956 | 11/2007 |
| WO | WO 2008/082282 | 7/2008 |
| WO | WO 2010/021718 | 2/2010 |
| WO | WO 2010/021720 | 2/2010 |
| WO | WO 2010/033240 | 3/2010 |

OTHER PUBLICATIONS

Kim, et al., "Synthetic dsRNA Dicer substrates enhance RNAi potency and efficacy", Nature Biotechnology, vol. 23, No. 2, pp. 222-226, (Feb. 2005).

Krutzfeldt, et al., "Silencing of microRNAs in vivo with antagomirs", Nature, vol. 438, pp. 685-689, (Dec. 2005).

Rose, et al., "Functional polarity is introduced by Dicer processing of short substrate RNAs", Nucleic Acids Research, vol. 33, No. 13, pp. 4140-4156, (2005).

Sadamoto, et al., "Control of Bacteria Adhesion by Cell-Wall Engineering", J. Am. Chem. Soc., vol. 126, pp. 3755-3761, (2004).

Zalipsky, "Chemistry of polyethylene glycol conjugates with biologically active molecules", Advanced Drug Delivery Reviews, vol. 16, pp. 157-182, (1995).

Zalipsky, et al., "Use of Functionalized Poly(Ethylene Glycol)s for Modification of Polypeptides", Poly(Ethylene Glycol) Chemistry: Biotechnical and Biomedical Applications, edited by J. Milton Harris, Plenum Press, NY, 13 pages, (1992).

PCT International Search Report and Written Opinion corresponding to PCT Application No. PCT/US2010/049179 date of mailing Jan. 19, 2011.

PCT Preliminary Report on Patentability corresponding to PCT Application No. PCT/US2010/049179 date of mailing Mar. 29, 2012.

Enzon Pharmaceuticals, Macromolecular Engineering Technologies, 16 pages, (2004).

NEKTAR™—Transforming Therapeutics, Nektar Molecule Engineering: Polyethylene Glycol and Derivatives for Advanced PEGylation, 24 pages, Catalog—2003, (Jul. 2003).

NEKTAR™—Transforming Therapeutics, Nektar Advanced PEGylation: Polyethylene Glycol and Derivatives for Advanced PEGylation, 27 pages, Catalog—2004, (Jul. 2004).

NEKTAR™—Transforming Therapeutics, Nektar Advanced PEGylation: Polyethylene Glycol and Derivatives for Advanced PEGylation, 33 pages, (Catalog 2005-2006).

NOF Corporation, PEG Derivatives, Phospholipid and Drug Delivery Materials for Pharmaceuticals, 46 pages, Catalogue 2003—$1^{st}$, (Jan. 2003).

NOF Corporation, PEG Derivatives, Phospholipid and Drug Delivery Materials for Pharmaceuticals, 27 pages, Catalogue 2003—$2^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; Biotins, 5 pages, (Apr. 2004).

Polypure Products, PEG amines; PEG acids and amino acids; PEG thiols and disulfides; Biotins, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog —(Jan. 2000).

Shearwater Corporation, Polyethylene Glycol and Derivatives for Biomedical Applications, 20 pages, Catalog—(Jul. 2001).

* cited by examiner

MONOCONJUGATED CHITOSANS AS DELIVERY AGENTS FOR SMALL INTERFERING NUCLEIC ACIDS

CROSS REFERENCE TO RELATED APPLICATIONS

This application is a 35 U.S.C. §371 application of International Application No. PCT/US2010/049179, filed Sep. 16, 2010, designating the United States, which claims the benefit of priority under 35 U.S.C. §119(e) to U.S. Provisional Patent Application No. 61/243,516, filed Sep. 17, 2009, the disclosures of which are incorporated herein by reference in their entireties.

FIELD OF THE INVENTION

Among other things, the present disclosure relates generally to complexes comprising a small interfering nucleic acid (siNA) and a polymer conjugate. With respect to the polymer conjugate, the polymer conjugate comprises a chitosan-water-soluble polymer conjugate. The disclosure further relates to compositions comprising the complexes, methods for preparing the complexes, and methods of administering such a composition.

BACKGROUND OF THE INVENTION

RNA interference (or "RNAi") is currently recognized as a highly specific mechanism of sequence-specific gene silencing. See deFougerolles et al. (2007) *Nature Reviews* 6:443-453. The mechanism allows for the specific and profound reduction of proteins and mRNA.

Briefly, the RNAi mechanism involves double-stranded RNA (dsRNA) intentionally synthesized with a sequence complementary to a gene of interest and subsequently introduced into a cell or organism, where the dsRNA is recognized as exogenous genetic material and activates the RNAi pathway. If the exogenous dsRNA is relatively long, it will be cleaved into small interfering RNAs (siRNAs). Alternatively, if the exogenous dsRNA is relatively short (about 30 base pairs or less), cleavage does not occur, the exogenous dsRNA itself acts as the siRNA substrate, and complications arising from activation of innate immunity defenses are avoided. In both cases, the siRNA becomes incorporated into an RNA-induced silencing complex (RISC) followed by unwinding of the double stranded siRNA into two strands. One of these strands, the "sense" strand (also known as the "passenger" strand), is discarded. The other strand, the "guide" strand (also known as the "antisense" strand) recognizes target sites to direct mRNA cleavage, thereby silencing its message. A similar RNAi mechanism involves microRNAs (miRNAs) deriving from imperfectly paired non-coding hairpin RNA structures.

Through the specific targeting of genes, RNAi-based therapies have the ability to substantially block the production of undesired proteins. Thus, in diseases and conditions attributable to the undesired or over expression of certain proteins, RNAi-based therapies represent a potentially powerful and important approach in medical therapies.

Despite the great promise of RNAi-based therapies, there remains a problem of the relative short half life of the small interfering nucleic acids "siNAs" used in RNAi-based approaches in vivo. Thus, there remains a need for better and improved versions of siNAs in order to bring the RNAi-based therapies to fruition.

Chitosan-PEG conjugates have been used as complexing agents for siRNA. See, for example, WO10/021,720 and WO10/021,718. In the studies described therein, PEG-chitosan conjugates were prepared by reaction of a PEG with an amine group on the chitosan. Because a chitosan molecule includes numerous amine groups, PEG molecules conjugated to these amine groups produce mixtures of PEGylated chitosans, each having a different number of PEG molecules conjugated to the chitosan and each generating different complexing properties. As a consequence, it is not possible to prepare a well defined product based on conjugating PEG to the numerous amine groups of chitosan. It would therefore be desirable to form a PEG-chitosan conjugate in which a single PEG molecule could be attached to the carbohydrate. Among other things, such a PEG-chitosan conjugate could be formed in a more uniform and consistent way, thereby having the advantage of (among other things) more uniform and consistent siNA compositions, including: (a) complexes of siNA and monoPEG-chitosan; and (b) conjugates of siNA wherein siNA is conjugated to monoPEG-chitosan. More uniform and consistent siNA compositions will have the advantages of more uniform and consistent performance, and (at least with respect to complexes) more stable complex formation.

SUMMARY OF THE INVENTION

In one or more embodiments of the invention, a conjugate is provided, the conjugate having a single water-soluble, non-peptidic polymer attached to a chitosan; exemplary conjugates of which are encompassed by the following structure:

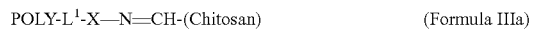

POLY-$L^1$-X—N=CH-(Chitosan)     (Formula IIIa)

wherein:

POLY is a water-soluble, non-peptidic polymer [and preferably is a poly(alkylene oxide) such as a PEG] optionally having a functional group, $G^2$, in protected or unprotected form, attached to it via a linker group (e.g., $L^3$);

$L^1$ is a linker group;

X is oxygen or $NR^2$, wherein $R^2$ is selected from the group consisting of hydrogen, methyl, lower alkyl, cycloalkyl, and aryl (and preferably $R^2$ is H or methyl); and Chitosan is a residue of a chitosan.

In one or more embodiments of Formula IIIa, it is preferred that X is oxygen or NH. The imine linkage within the compounds of Formula IIIa can be converted into the corresponding amine using conventional reducing techniques, thereby providing conjugates encompassed by the following structure:

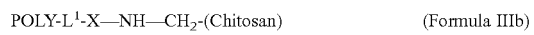

POLY-$L^1$-X—NH—$CH_2$-(Chitosan)     (Formula IIIb)

wherein each of POLY, $L^1$, X and Chitosan is as defined with respect to Formula IIIa.

In one or more embodiments of each of Formulae IIIa and IIIb, the POLY moiety also bears a functional group, $G^2$, e.g., a functional group that is reactive to an amine, thiol or a hydroxyl group of an siNA, the functional group being in protected or unprotected form, which functional group-bearing embodiments of Formulae IIIa and IIIb, are encompassed by the following structures:

$G^2$-$L^3$-POLY-$L^1$-X—N=CH-(Chitosan)     (Formula IIIc)

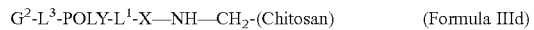

$G^2$-$L^3$-POLY-$L^1$-X—NH—$CH_2$-(Chitosan)     (Formula IIId)

wherein each of POLY, $L^1$, X and Chitosan are as defined with respect to Formula IIIa, and further wherein $L^3$ is a linker group and $G^2$ is a functional group, in protected or unprotected form.

In one or more embodiments of the invention, a monoPEGylated chitosan conjugate is provided.

In one or more embodiments of the invention, a composition is provided, the composition comprising a plurality of chitosan-water-soluble, non-peptidic polymer conjugates, wherein greater than about 30% (preferably greater than about 50%, more preferably greater than about 60%, still more preferably greater than about 70%, still more preferably greater than about 80%, still more preferably greater than 85%, still more preferably greater than about 90%, still more preferably greater than about 95%, and still more preferably greater than about 98%) of all chitosans in the composition are in the form of a conjugate having a single water-soluble, non-peptidic polymer attached to the chitosan.

In one or more embodiments of the invention, a complex is provided, the complex comprising siNA complexed with a plurality of conjugates, each conjugate in the plurality having a single water-soluble, non-peptidic polymer attached to a chitosan.

In one or more embodiments of the invention, a complex is provided, the complex comprising siNA complexed with a plurality of monoPEGylated chitosan conjugates.

In one or more embodiments of the invention, a method is provided, the method comprising reacting a nucleophile-terminated, water-soluble, non-peptidic polymer (such as a PEG bearing a highly nucleophilic amine such as an oxyamine or hydrazine) with a chitosan. The conjugation takes place at a chitosan's lone aldehyde, a functional group of chitosan that is in equilibrium in liquid with the corresponding lone hydroxyl-bearing cyclic acetal of chitosan.

Using this method, a conjugate having a single water-soluble, non-peptidic polymer attached to a chitosan can be prepared. In some instances, the nucleophile-terminated, water-soluble, non-peptidic polymer has, in addition to a terminus bearing a nucleophile, one or more additional termini, each of the one more additional termini bearing a functional group, either the same or different as the nucleophile and either in protected or in unprotected form.

In one or more embodiments of the invention, a nucleophile-terminated, water-soluble, non-peptidic polymer is provided, the nucleophile-terminated, water-soluble, non-peptidic polymer having the following structure:

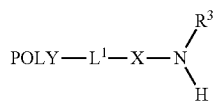
(Formula Ia)

wherein:
POLY is a water-soluble, non-peptidic polymer [and preferably is a poly(alkylene oxide) such as a PEG] optionally having a functional group, $G^2$, attached to it via a linker group (e.g., $L^3$);
$L^1$ is a linker group;
X is oxygen or $NR^2$, wherein $R^2$ is selected from the group consisting of hydrogen, methyl, lower alkyl, cycloalkyl, and aryl (and preferably $R^2$ is H or methyl); and
$R^3$ is H or methyl (and is preferably H).
In one or more embodiments of Formula I, it is preferred that X is oxygen or NH. In one or more embodiments of Formula Ia, the water-soluble, non-peptidic also bears a functional group, $G^2$, e.g., a functional group that is reactive to an amine or a hydroxyl group of an siNA, the functional group being in protected or unprotected form, which embodiments functional group-bearing embodiments of Formula Ia are encompassed by the following structure:

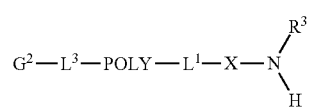
(Formula Ib)

wherein each of POLY, $L^1$, X and $R^3$ are as defined with respect to Formula Ia, and further wherein $L^3$ is a linker group and $G^2$ is a functional group, in protected or unprotected form.

In one or more embodiments of the invention, a method is provided, the method comprising reacting a nucleophile-terminated, heterofunctional reagent with a chitosan. In those instances where the nucleophile-terminated, heterofunctional reagent bears a functional group, e.g., "$G^1$", the method results in a chitosan bearing the functional group, e.g., "$G^1$". The nucleophile-terminated, heterofunctional reagent can contain a first functional group and a second function group that is different from the first functional group; such a nucleophile-terminated, heterofunctional reagent is understood to be a "nucleophile-terminated, heterobifunctional reagent." Exemplary nucleophile-terminated, heterobifunctional reagents are encompassed by the following structure:

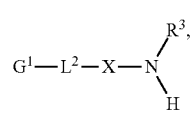
(Formula II)

wherein:
$G^1$ is a functional group, in protected or unprotected form, and different from

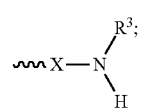

$L^2$ is a linker group;
X is oxygen or $NR^2$, wherein $R^2$ is selected from the group consisting of hydrogen, methyl, lower alkyl, cycloalkyl, and aryl (and preferably $R^2$ is H or methyl); and
$R^3$ is H or methyl (and is preferably H).
In one or more embodiments of Formula II, it is preferred that X is oxygen or NH.

In one or more embodiments of the invention, a chitosan bearing a functional group, e.g., $G^1$, is provided, the chitosan bearing a functional group, e.g., $G^1$, has the following structure:

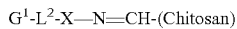
$G^1$-$L^2$-X—N=CH-(Chitosan)  (Formula IVa)

wherein:
$G^1$ is a functional group, in protected or unprotected form;
$L^2$ is a linker group;
X is oxygen or $NR^2$, wherein $R^2$ is selected from the group consisting of hydrogen, methyl, lower alkyl, cycloalkyl, and aryl (and preferably $R^1$ is H or methyl); and
Chitosan is a residue of a chitosan.
Moreover, the imine linkage within the compounds of Formula IVa can be converted into the corresponding amine using conventional reducing techniques, thereby providing chitosans bearing a functional group encompassed by the following structure:

wherein each of $G^1$, $L^2$, X and Chitosan is as defined with respect to Formula IVa.

The chitosans bearing a functional group, $G^1$, (e.g., compounds encompassed by Formulae IVa and IVb) can be used in a reaction (following deprotecting if the functional group is in protected form) with a water-soluble, non-peptidic polymer reagent bearing a functional group that is reactive with functional group, $G^1$, to provide another embodiment of a single water-soluble, non-peptidic polymer attached to a chitosan. In such an embodiment, exemplary chitosan-water-soluble, non-peptidic polymer conjugates are encompassed by one of the following structures:

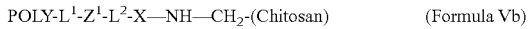

wherein (for each of Formulae Va and Vb)
POLY is a water-soluble, non-peptidic polymer [and preferably is a poly(alkylene oxide) such as a PEG];
$L^1$ is a linker group;
$Z^1$ is a linkage resulting from the reaction of the functional group from the chitosan bearing a functional group, $G^1$, and the functional group of the water-soluble, non-peptidic polymer reagent bearing a functional group that is reactive with functional group, $G^1$;
$L^2$ is a linker group;
X is oxygen or $NR^2$, wherein $R^2$ is selected from the group consisting of hydrogen, methyl, lower alkyl, cycloalkyl, and aryl (and preferably $R^2$ is H or methyl); and
Chitosan is a residue of a chitosan.

Optionally, the water-soluble, non-peptidic polymer reagent bearing a functional group that is reactive with functional group, $G^1$, also bears a second functional group, $G^2$, that may be the same or different from $G^1$, and in each case, may be in protected or unprotected form. Exemplary water-soluble, non-peptidic polymer reagents bearing a functional group that is reactive with functional group, $G^1$, and bears a second functional group, $G^2$, are encompassed by the following structures:

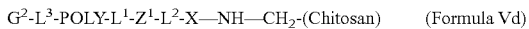

wherein (for each of Formulae Vc and Vd):
$G^2$ is a functional group, in protected or unprotected form;
$L^3$ is a linker group;
POLY is a water-soluble, non-peptidic polymer [and preferably is a poly(alkylene oxide) such as a PEG];
$L^1$ is a linker group;
$Z^1$ is a linkage (resulting from the reaction of the functional group from the chitosan bearing a functional group, G, and the functional group of the water-soluble, non-peptidic polymer reagent bearing a functional group that is reactive with functional group, $G^1$);
$L^2$ is a linker group;
X is oxygen or $NR^2$, wherein $R^2$ is selected from the group consisting of hydrogen, methyl, lower alkyl, cycloalkyl, and aryl (and preferably $R^2$ is H or methyl); and
Chitosan is a residue of a chitosan.

In one or more embodiments of the invention, an siNA conjugate of: (a) an siNA; and (b) a single water-soluble, non-peptidic polymer attached to a chitosan, is provided. In such an embodiment, exemplary siNA conjugates are encompassed by one of the following structures:

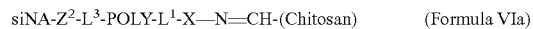

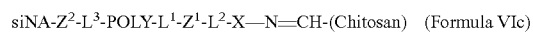

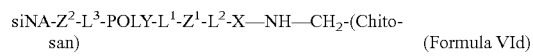

wherein:
siNA is a residue of an siNA (wherein the siNA has a functional group, e.g., an amine, thiol, or hydroxyl group, suitable for reacting with another functional group to form a covalent bond);
$Z^2$ is a linkage (resulting from the reaction of a functional group from the siNA and a functional group associated with the water-soluble, non-peptidic polymer attached to a chitosan of the water-soluble, non-peptidic polymer);
$L^3$ is a linker group;
POLY is a water-soluble polymer [and preferably is a poly(alkylene oxide) such as a PEG];
$L^1$ is a linker group;
X is oxygen or $NR^2$, wherein $R^2$ is selected from the group consisting of hydrogen, methyl, lower alkyl, cycloalkyl, and aryl (and preferably $R^2$ is H or methyl); and
Chitosan is a residue of a chitosan,
and further wherein (for each of Formulae VIc and VId):
$Z^1$ is a linkage (resulting from the reaction of the functional group from the chitosan bearing a functional group, $G^1$, and the functional group of the water-soluble, non-peptidic polymer reagent bearing a functional group that is reactive with functional group, $G^1$); and
$L^2$ is a linker group.

In one or more embodiments of the invention, a method for preparing an siNA conjugate encompassed by any one of Formulae VIa, VIb, VIc and VId is provided, the method comprising combining under conjugation conditions an siNA with a compound encompassed by Formulae IIIc, IIId, VIc and VId, respectfully, in which the functional group, $G^1$, is unprotected form.

Other aspects of the invention are directed to the provision of complexes further comprise a transfecting agent. Also provided are compositions comprising complexes, having the same or different siNAs, and methods for administering such complexes to a subject.

These and other aspects of the invention will become apparent upon review of the following description.

DETAILED DESCRIPTION OF THE INVENTION

Before describing the present invention in detail, it is to be understood that this invention is not limited to particular polymers, synthetic techniques, active agents, and the like, as such may vary.

As used in this specification and in the claims, the singular forms "a", "an", and "the" include plural referents unless the context clearly dictates otherwise. Thus, for example, reference to "a polymer" includes a single polymer as well as two or more of the same or different polymers, reference to "a conjugate" refers to a single conjugate as well as two or more of the same or different conjugates, reference to "an excipient" includes a single excipient as well as two or more of the same or different excipients, and the like.

"Optional" and "optionally" mean that the subsequently described circumstance may or may not occur, so that the description includes instances where the circumstance occurs and instances where it does not.

In describing and claiming the present invention, the following terminology will be used in accordance with the definitions described below.

"PEG", "polyethylene glycol" and "poly(ethylene glycol)" as used herein, are meant to encompass any water-soluble poly(ethylene oxide). Typically, PEGs comprise the following structure "—O($CH_2CH_2O)_m$—" where (m) is 2 to 4000. As used herein, PEG also includes "—($CH_2CH_2O)_m$—" and "—$CH_2CH_2$—O($CH_2CH_2O)_m$—$CH_2CH_2$—", depending upon whether or not the terminal oxygens have been displaced. When the PEG further comprises a linker group (to be described in greater detail below), the atoms comprising the linker group, when covalently attached to a water-soluble polymer segment, do not result in the formation of an oxygen-oxygen bond (i.e., an "—O—O—" or peroxide linkage). The term "PEG" includes structures having various terminal or "end capping" groups and so forth. The term "PEG" also means a polymer that contains a majority, that is to say, greater than 50%, of —$CH_2CH_2O$— monomeric subunits. With respect to specific forms, the PEG can take any number of a variety of molecular weights, as well as structures or geometries such as "branched," "linear," "forked," "multi-functional," "dendrimeric," and the like.

The terms "end-capped" or "terminally capped" are interchangeably used herein to refer to a terminal or endpoint of a polymer having an end-capping moiety. Typically, although not necessarily, the end-capping moiety comprises a hydroxy or $C_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled to can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like.

"Non-naturally occurring", with respect to a polymer or water-soluble polymer, indicates that the polymer in its entirety is not found in nature. A non-naturally occurring polymer or water-soluble polymer may, however, contain one or more subunits or portions of a subunit that are naturally occurring, so long as the overall polymer structure is not found in nature.

A "water-soluble polymer" is any polymer that is soluble in water at room temperature. Typically, a water-soluble polymer will transmit at least about 75%, more preferably at least about 95% of light, transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is still more preferred, however, that the water-soluble polymer is about 95% (by weight) soluble in water and most preferred that the water-soluble polymer is completely soluble in water.

When one component is "attached through one or more atoms," the "one or more atoms" can be a divalent water-soluble polymer, such as a poly(ethylene oxide) having a molecular weight of about 20,000 Daltons.

"Molecular weight," in the context of a water-soluble polymer of the invention, such as PEG, can be expressed as either a number average molecular weight or a weight average molecular weight. Unless otherwise indicated, all references to molecular weight herein refer to the weight average molecular weight. Both molecular weight determinations, number average and weight average, can be made using gel permeation chromatography or other liquid chromatography techniques. Other methods for measuring molecular weight can also be used, such as end-group analysis or colligative properties (e.g., freezing-point depression, boiling-point elevation, or osmotic pressure) to determine number average molecular weight, or light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

An "organic radical" as used includes, for example, alkyl, substituted alkyl, alkenyl, substituted alkenyl, alkynyl, substituted alkynyl, aryl and substituted aryl.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include ethyl, propyl, butyl, pentyl, isooctyl, decyl, 3-ethyl-3-pentyl, 2-methyl-1-hexyl, and the like. As used herein, "alkyl" includes cycloalkyl, when three or more carbon atoms are referenced, and lower alkyl. "Alkylene" refers to an unsaturated bivalent radical (e.g. —$(CH_2)_n$—.

"Lower alkyl" refers to an alkyl group containing from 1 to 6 carbon atoms, preferably 1 to 4 carbon atoms, and may be straight chain or branched, as exemplified by methyl, ethyl, n-butyl, iso-butyl, and tert-butyl. When a group is defined as "alkyl" herein, lower alkyl is generally a preferred embodiment.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Alkoxy" refers to an —O—R group, wherein R is alkyl or substituted alkyl, preferably $C_1$-$C_{20}$ alkyl (e.g., methoxy, ethoxy, propyloxy, benzyl, perfluorobutyl, etc.), preferably $C_1$-$C_7$ alkyl, more preferably $C_1$-$C_7$ alkyl. "Alkoxyalkyl" refers to an —R—O—R group, where R is as defined above, and is preferably unsubstituted $C_1$-$C_7$ alkyl.

"Aminoalkyl" refers to an —NHR or —$NR_2$ group, where R is alkyl as defined above, and is preferably unsubstituted $C_1$-$C_7$ alkyl, and the two R groups in —$NR_2$ may be the same or different. The two R groups may also form a five- to seven-membered ring.

"Iminoalkyl(ene)" refers to an —R'—N=R" group, where R" represents $CH_2$, CHR, or $CR_2$, where each R is alkyl as defined above, and the two R groups in —$CR_2$ may be the same or different. R' is alkyl as defined above, i.e., an $sp^2$ hybridized carbon, or alkylene, i.e., an $sp^2$ hybridized carbon forming one member of a double bond. An R in CHR or $CR_2$ taken together with the R" may form a five- to seven-membered ring.

As used herein, "alkenyl" refers to a branched or unbranched hydrocarbon group of 2 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-butynyl, isopentynyl, octynyl, decynyl, and so forth.

"Aliphatic" refers to a group containing carbon and hydrogen which is not aromatic. As used herein, it can refer to linear, branched, or cyclic groups. It can refer to saturated or unsaturated groups, with saturated groups generally being preferred.

"Aryl" means one or more aromatic rings, each of 5 or 6 core carbon atoms. Aryl includes multiple aryl rings that may be fused, as in naphthyl, or unfused, as in biphenyl. Aryl rings may also be fused or unfused with one or more cyclic hydrocarbon, heteroaryl, or heterocyclic rings. As used herein, "aryl" includes heteroaryl. An aromatic moiety (e.g., $Ar^1$, $Ar^2$, and so forth), means a structure containing aryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Non-interfering substituents" are those groups that, when present in a molecule, are typically non-reactive with other functional groups contained within the molecule. Such groups include: lower alkyl, lower alkoxy, $C_3$-$C_8$ cycloalkyl, e.g., cyclopropyl, cyclobutyl, and the like; halo, e.g., fluoro, chloro, bromo, and iodo; cyano; phenyl; substituted phenyl; and the like. For substitutions on a phenyl ring, the substituents may be in any orientation (i.e., ortho, meta, or para). Preferred non-interfering substituents include lower alkyl, lower alkoxy, cyclopropyl, fluoro, chloro, and cyano.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl (e.g., 0-2 substituted phenyl); substituted phenyl; and the like. "Substituted aryl" is aryl having one or more non-interfering groups as a substituent. For substitutions on a phenyl ring, the substituents may be in any orientation (i.e., ortho, meta, or para).

As used herein, the "halo" designator (e.g., fluoro, chloro, iodo, bromo, and so forth) is generally used when the halogen is attached to a molecule, while the suffix "ide" (e.g., fluoride, chloride, iodide, bromide, and so forth) is used when the halogen exists in its independent ionic form (e.g., such as when a leaving group leaves a molecule).

"Electrophile" refers to an ion or atom or collection of atoms, that may be ionic, having an electrophilic center, i.e., a center that is electron seeking, capable of reacting with a nucleophile.

"Nucleophile" refers to an ion or atom or collection of atoms that may be ionic having a nucleophilic center, i.e., a center that is seeking an electrophilic center or with an electrophile.

A basic or acidic reactant described herein includes neutral, charged, and any corresponding salt forms thereof.

As used herein, the term "carboxylic acid" is a moiety having a —C(O)OH functional group, as well as moieties that are derivatives of a carboxylic acid, such derivatives including, for example, protected carboxylic acids. Thus, unless the context clearly dictates otherwise, the term carboxylic acid includes not only the acid form, but corresponding esters and protected forms as well. With regard to protecting groups suited for a carboxylic acid and any other functional group described herein, reference is made to Greene et al., "PROTECTIVE GROUPS IN ORGANIC SYNTHESIS", $3^{rd}$ Edition, John Wiley and Sons, Inc., New York, 1999.

The term "reactive" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected" or "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive functional group being protected as well as the reaction conditions to be employed and the presence of additional reactive or protecting groups in the molecule, if any. Protecting groups known in the art, as well as methods for protecting and deprotecting functional groups, can be found in Greene et al., supra.

As used herein, the term "functional group" or any synonym thereof is meant to encompass protected forms thereof. In particular, recitation of specific functional groups such as carboxylic acids, aldehydes, or hydroxyl groups encompasses protected forms thereof.

"Multifunctional", in the context of a polymer of the invention, means a polymer having 3 or more functional groups contained therein, where the functional groups may be the same or different. Multifunctional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer. A "difunctional" polymer means a polymer having two functional groups contained therein, either the same (i.e., homodifunctional) or different (i.e., heterodifunctional).

"Branched," in reference to the geometry or overall structure of a polymer, refers to polymer having 2 or more polymer "arms." A branched polymer may possess 2 polymer arms, 3 polymer arms, 4 polymer arms, 6 polymer arms, 8 polymer arms or more. One particular type of highly branched polymer is a dendritic polymer or dendrimer, which, for the purposes of the invention, is considered to possess a structure distinct from that of a branched polymer.

A "dendrimer" or dendritic polymer is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

In the context of the present description, the definition of a variable provided with respect to one structure or formula is applicable to the same variable repeated in a different structure, unless the context dictates otherwise. Thus, for example, the definition of "POLY," "linker group," "X" and so forth with respect to a polymer can be equally applicable to a water-soluble polymer conjugate provided herein.

The terms "linker" and "linker group" (which may also be referred to as a spacer or spacer moiety) are used herein to refer to an atom or a collection of atoms optionally used to link one moiety to another, such as a water-soluble polymer to an siNA. The linker groups are preferably hydrolytically stable but may include one or more physiologically hydrolyzable or enzymatically releasable linkages. Exemplary spacer moieties are described further below.

A "hydrolyzable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, ortho esters, peptides and oligonucleotides.

A "releasable linkage" includes, but is not limited to, a physiologically cleavable bond, a hydrolyzable bond, and an enzymatically releasable linkage. Thus, a "releasable linkage" is a linkage that may undergo either hydrolysis or cleavage by some other mechanism (e.g., enzyme-catalyzed, acid-catalyzed, base-catalyzed, and so forth) under physiological conditions.

An "enzymatically releasable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes (carbamates), and the like. Generally, a hydrolytically stable linkage is one that exhibits a rate of hydrolysis of less than about 1-2% per day under physiological conditions. Hydrolysis rates of representative chemical bonds can be found in most standard chemistry textbooks. It must be pointed out that some linkages can be hydrolytically stable or hydrolyzable, depending upon (for example) adjacent and neighboring atoms and ambient conditions. One of ordinary skill in the art can determine whether a given linkage or bond is hydrolytically stable or hydrolyzable in a given context by, for example, placing a linkage-containing molecule of interest under conditions of interest and testing for evidence of hydrolysis (e.g., the presence and amount of two molecules resulting from the cleavage of a single molecule). Other approaches known to those of ordinary skill in the art for determining whether a given linkage or bond is hydrolytically stable or hydrolyzable can also be used.

The terms "active agent," "biologically active agent" and "pharmacologically active agent" are used interchangeably herein and are defined to include any agent, drug, compound, composition of matter or mixture that provides some pharmacologic, often beneficial, effect that can be demonstrated in-vivo or in vitro. This includes foods, food supplements, nutrients, nutriceuticals, drugs, proteins, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a polymer-active agent conjugate, typically present in a pharmaceutical preparation, that is needed to provide a desired level of active agent and/or conjugate in the bloodstream or in a target tissue. The exact amount will depend upon numerous factors, e.g., the particular active agent, the components and physical characteristics of the pharmaceutical preparation, intended patient population, patient considerations, and the like, and can readily be determined by one of ordinary skill in the art, based upon the information provided herein and available in the relevant literature.

The terms "patient" and "subject" refer to a living organism suffering from or prone to a condition that can be prevented or treated by administration of a conjugate as provided herein, and includes both humans and animals.

By "inhibit" or "down regulate" it is meant that the activity of a gene expression product or level of RNAs or equivalent RNAs encoding one or more gene products is reduced below that observed in the absence of the nucleic acid molecule. In one embodiment, inhibition with a siRNA molecule preferably is below that level observed in the presence of an inactive or attenuated molecule that is unable to mediate an RNAi response. In another embodiment, inhibition of gene expression with the siRNA molecule included as part of the instant invention is greater in the presence of the siRNA molecule than in its absence.

By "RNA" is meant a molecule comprising at least one ribonucleotide residue. By "ribonucleotide" is meant a nucleotide with a hydroxyl group at the 2' position of a β-D-ribofuranose moiety. The terms include triple-stranded RNA, double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a siRNA or internally (e.g. capped structures), for example, at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "gene" and "target gene" and "target nucleic acid" is meant, a nucleic acid that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus.

As indicated above, the invention provides, among other things, a method for monofunctionalization of chitosan, a carbohydrate polymer formed by deacetylation of the naturally occurring chitin. As used herein, the concept of chitosan "monoderivatized" and "monofunctonalized" means that a chitosan is modified such that it has, at a single location within the entire chitosan molecule, a water-soluble, non-peptidic polymer attached thereto. When the water-soluble, non-peptidic polymer is a PEG, such a monofunctionalized chitosan can be referred to as "monoPEGylated chitosan" or a "monoPEGylated chitosan conjugate."

Thus, exemplary monofunctionalized compounds of the invention are encompassed within the following structures:

POLY-L$^1$-X—N=N=CH-(Chitosan)  (Formula IIIa)

and its corresponding reduced version

POLY-L$^1$-X—NH—CH$_2$-(Chitosan),  (Formula IIIb)

as well as

POLY-L$^1$-Z$^1$-L$^2$-X—N=CH-(Chitosan)  (Formula Va)

and its corresponding reduced version

POLY-L$^1$-Z$^1$-L$^2$-X—NH—CH$_2$-(Chitosan),  (Formula Vb)

wherein for each of Formulae IIIa, IIIb, Va and Vb:
POLY is a water-soluble, non-peptidic polymer [and preferably is a poly(alkylene oxide) such as a PEG];
L$^1$ is a linker group;
X is oxygen or NR$^2$, wherein R$^2$ is selected from the group consisting of hydrogen, methyl, lower alkyl, cycloalkyl, and aryl (and preferably R$^2$ is H or methyl); and
Chitosan is a residue of a chitosan,
and further wherein for Formulae Va and Vb:
L$^2$ is a linker group;
Z$^1$ is a linkage (resulting from the reaction of the functional group from a chitosan bearing a functional group, G$^1$, and a functional group of a water-soluble, non-peptidic polymer reagent bearing a functional group that is reactive with functional group, G$^1$).

These and other monofunctionalized chitosans encompassed within the invention can be used in the preparation of complexes that comprise a plurality of monofunctionalized chitosans and siNA.

In addition to forming complexes, the monofunctionalized chitosans can also be covalently attached or conjugated to siNA. In one approach, the water-soluble, non-peptidic polymer used in preparing the monofunctionalized chitosan is selected so as to include a functional group, G$^2$, thereby resulting in a monofunctionalized chitosan that also bears the functional group, G$^2$. Such a functional group-bearing monofunctionalized chitosan can be conjugated to siNA. Exemplary functional group-bearing monofunctionalized chitosans are encompassed within the following structures:

G$^2$-L$^3$-POLY-L$^1$-X—N=CH-(Chitosan)  (Formula IIIc)

G$^2$-L$^3$-POLY-L$^1$-X—NH—CH$_2$-(Chitosan)  (Formula IIId)

G$^2$-L$^3$-POLY-L$^1$-Z$^1$-L$^2$-X—N=CH—(Chitosan)  (Formula Vc)

G$^2$-L$^3$-POLY-L$^1$-Z$^1$-L$^2$-X—NH—CH$_2$-(Chitosan)  (Formula Vd)

wherein for each of Formulae IIIc, IIId, Vc and Vd:
G$^2$ is a functional group, in protected or unprotected form;
L$^3$ is a linker group;
POLY is a water-soluble, non-peptidic polymer [and preferably is a poly(alkylene oxide) such as a PEG];
L$^1$ is a linker group;
X is oxygen or NR$^2$, wherein R$^2$ is selected from the group consisting of hydrogen, methyl, lower alkyl, cycloalkyl, and aryl (and preferably R$^2$ is H or methyl); and
Chitosan is a residue of a chitosan,
and for each of Formulae Vc and Vd:
Z$^1$ is a linkage (resulting from the reaction of the functional group from the chitosan bearing a functional group, G$^1$, and the functional group of the water-soluble, non-peptidic polymer reagent bearing a functional group that is reactive with functional group, G$^1$);
L$^2$ is a linker group.

Exemplary siNA conjugates are encompassed by one of the following structures:

siNA-Z$^2$-L$^3$-POLY-L$^1$-X—N=CH-(Chitosan)  (Formula VIa)

siNA-Z$^2$-L$^3$-POLY-L$^1$-X—NH—CH$_2$-(Chitosan)  (Formula VIb)

siNA-Z$^2$-L$^3$-POLY-L$^1$-Z$^1$-L$^2$-X—N=CH-(Chitosan)  (Formula VIc)

siNA-Z$^2$-L$^3$-POLY-L$^1$-Z-L$^2$-X—NH—CH$_2$-(Chitosan)  (Formula VId)

wherein:
siNA is a residue of an siNA (wherein the siNA has a functional group, e.g., an amine, thiol or hydroxyl group, suitable for reacting with another functional group to form a covalent bond);
Z$^2$ is a linkage (resulting from the reaction of a functional group from the siNA and a functional group associated with the water-soluble, non-peptidic polymer attached to a chitosan of the water-soluble, non-peptidic polymer);
L$^3$ is a linker group;
POLY is a water-soluble, non-peptidic polymer [and preferably is a poly(alkylene oxide) such as a PEG];
L$^1$ is a linker group;
X is oxygen or NR$^2$, wherein R$^2$ is selected from the group consisting of hydrogen, methyl, lower alkyl, cycloalkyl, and aryl (and preferably R$^2$ is H or methyl); and
Chitosan is a residue of a chitosan,
and further wherein (for each of Formulae VIc and VId):
Z$^1$ is a linkage (resulting from the reaction of the functional group from the chitosan bearing a functional group, G$^1$, and the functional group of the water-soluble, non-peptidic polymer reagent bearing a functional group that is reactive with functional group, G$^1$); and
L$^2$ is a linker group.

In one approach for preparing a monofunctionalized chitosan as described herein, a nucleophile-terminated, water-soluble, non-peptidic polymer is combined under suitable conjugation conditions with the reductive end of chitosan. The preferable nucleophile is an oxyamine or hydrazine. Exemplary nucleophile-terminated, water-soluble, non-peptidic polymers are encompassed by one of the following structures:

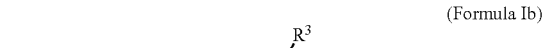
(Formula Ia)

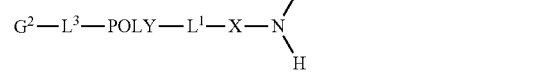
(Formula Ib)

wherein for each of Formulae Ia and Ib:
POLY is a water-soluble, non-peptidic polymer [and preferably is a poly(alkylene oxide) such as a PEG] and when the optional functional group is present as provided in Formula Ib, a functional group, G$^2$, in protected or unprotected form, attached to it via a linker group, e.g., L$^3$;
L$^1$ is a linker group;

X is oxygen or NR², wherein R² is selected from the group consisting of hydrogen, methyl, lower alkyl, cycloalkyl, and aryl (and preferably R² is H or methyl); and R³ is H or methyl (and is preferably H).

In another approach for preparing a monofunctionalized chitosan as described herein, a nucleophile-terminated, heterofunctional reagent is first conjugated to a chitosan to provide chitosan bearing a functional group, e.g., G¹, which chitosan bearing a functional group, e.g., G¹, is thereafter used in a conjugation reaction with a water-soluble, non-peptidic polymer.

Exemplary nucleophile-terminated, heterobifunctional reagents are encompassed by the following structure:

(Formula II)

wherein:

G¹ is a functional group, in protected or unprotected form, and different from

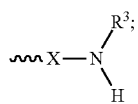

L² is a linker group;

X is oxygen or NR², wherein R² is selected from the group consisting of hydrogen, methyl, lower alkyl, cycloalkyl, and aryl (and preferably R² is H or methyl); and R³ is H or methyl (and is preferably H).

In one or more embodiments of Formula II, it is preferred that X is oxygen or NH.

In one or more embodiments of the invention, a chitosan bearing a functional group, e.g., G¹, is provided, the chitosan bearing a functional group, e.g., G¹, has the following structure:

G¹-L²-X—N=CH-(Chitosan)　　　(Formula IVa)

wherein:

G¹ is a functional group, in protected or unprotected form;
L² is a linker group;
X is oxygen or NR², wherein R² is selected from the group consisting of hydrogen, methyl, lower alkyl, cycloalkyl, and aryl (and preferably R² is H or methyl); and
Chitosan is a residue of a chitosan.

Moreover, the imine linkage within the compounds of Formula IVa can be converted into the corresponding amine using conventional reducing techniques, thereby providing chitosans bearing a functional group encompassed by the following structure:

G¹-L²-X—NH—CH₂-(Chitosan)　　　(Formula IVb)

wherein each of G¹, L², X and Chitosan is as defined with respect to Formula IVa.

The chitosans bearing a functional group, G¹ (e.g., compounds encompassed by Formulae IVa and IVb), can be used in a reaction (following deprotecting if the functional group is in protected form) with a water-soluble, non-peptidic polymer reagent bearing a functional group that is reactive with functional group, G¹ (but substantially unreactive with other functional groups present on the chitosan), to provide another embodiment of a single water-soluble, non-peptidic polymer attached to a chitosan. In such an embodiment, exemplary chitosan-water-soluble, non-peptidic polymer conjugates are encompassed by one of the following structures:

POLY-L¹-Z¹-L²-X—N=CH-(Chitosan)　　　(Formula Va)

POLY-L¹-Z¹-L²-X—NH—CH₂-(Chitosan)　　　(Formula Vb)

wherein (for each of Formulae Va and Vb):

POLY is a water-soluble, non-peptidic polymer [and preferably is a poly(alkylene oxide) such as a PEG];
L¹ is a linker group;
Z¹ is a linkage resulting from the reaction of the functional group from the chitosan bearing a functional group, G¹, and the functional group of the water-soluble, non-peptidic polymer reagent bearing a functional group that is reactive with functional group, G¹;
L² is a linker group;
X is oxygen or NR², wherein R² is selected from the group consisting of hydrogen, methyl, lower alkyl, cycloalkyl, and aryl (and preferably R² is H or methyl); and
Chitosan is a residue of a chitosan.

Optionally, the water-soluble, non-peptidic polymer reagent bearing a functional group that is reactive with functional group, G¹, also bears a second functional group, G², that may be the same or different from G¹, and in each case, may be in protected or unprotected form. In instances where such a water-soluble, non-peptidic polymer is used to conjugate the water-soluble, non-peptidic polymer to a chitosan bearing a functional group, the functional group that is reactive with functional group, G¹ on the chitosan is substantially unreactive with other functional groups present on the chitosan and second functional group is either in protected form or is substantially unreactive G¹ and other functional groups present on the chitosan. Exemplary water-soluble, non-peptidic polymer reagents bearing a functional group that is reactive with functional group, G¹, and bears a second functional group, G², are encompassed by the following structures:

G²-L³-POLY-L¹-Z¹-L²-X—N=CH-(Chitosan)　　　(Formula Vc)

G²-L³-POLY-L¹-Z¹-L²-X—NH—CH₂-(Chitosan)　　　(Formula Vd)

wherein (for each of Formulae Vc and Vd):

G² is a functional group, in protected or unprotected form;
L³ is a linker group;
POLY is a water-soluble polymer [and preferably is a poly(alkylene oxide) such as a PEG];
L¹ is a linker group;
Z¹ is a linkage (resulting from the reaction of the functional group from the chitosan bearing a functional group, G¹, and the functional group of the water-soluble, non-peptidic polymer reagent bearing a functional group that is reactive with functional group, G¹);
L² is a linker group;
X is oxygen or NR², wherein R² is selected from the group consisting of hydrogen, methyl, lower alkyl, cycloalkyl, and aryl (and preferably R² is H or methyl); and
Chitosan is a residue of a chitosan.

As described above, the monofunctionalized chitosan, chitosan bearing a functional group, siNA conjugates, heterofunctional reagents, and so forth, include one or more linker groups (e.g., L¹, L², L³, and so forth).

A linker group is typically but is not necessarily linear in nature. The overall length of the linker group will typically range between 1 to about 40 atoms, where by length is meant the number of atoms in a single chain, not counting substituents. For instance, —$CH_2$— counts as one atom with respect to overall linker length, and —$CH_2CH(CH_3)O$— counts as 3 atoms in length. Preferably, a linker group will have a length of about 1 to about 20 atoms, and, more preferably, from about 2 to about 15 atoms, e.g., 3 to 8 atoms. In some instances, a given linker in the Formulae provided herein will not have any atoms and will simply represent a covalent bond.

Illustrative linker groups include, but are not limited to —$(CH_2)_c$-$D_e$-$(CH_2)_f$— and —$(CH_2)_p$-$M_r$-$C(O)$-$K_s$-$(CH_2)_q$— where c is 0 to 8; D is O, NH, or S; e is 0 or 1; f is 0 to 8; p is 0 to 8; M is NH or O; K is NH or O; q is 0 to 8, and r and s are each independently 0 or 1, —O—, —S—, —C(O)—, —S($O_2$)—, —S(O)—, —NH—S($O_2$)—, —S($O_2$)—NH—, —CH=CH—, —O—CH=CH—, —C(O)—NH—, —NH—C(O)—NH—, —O—C(O)—NH—, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —S—$CH_2$—, —$CH_2$—S—, —S—$CH_2$—$CH_2$—, —$CH_2$—S—$CH_2$—, —$CH_2$—$CH_2$—S—, —S—$CH_2$—$CH_2$—$CH_2$—, —$CH_2$—S—$CH_2$—$CH_2$—, —$CH_2$—$CH_2$—S—$CH_2$—, —$CH_2$—$CH_2$—$CH_2$—S—, —S—$CH_2$—$CH_2$—$CH_2$—$CH_2$—, —$CH_2$—S—$CH_2$—$CH_2$—$CH_2$—, —$CH_2$—$CH_2$—S—$CH_2$—$CH_2$—, —$CH_2$—$CH_2$—$CH_2$—S—$CH_2$—, —$CH_2$—$CH_2$—$CH_2$—$CH_2$—S—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, —C(O)—NH—$CH_2$—$CH_2$—$CH_2$—$CH_2$—, —$CH_2$—C(O)—NH—$CH_2$—$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—$CH_2$—$CH_2$—C(O)—NH—, —NH—C(O)—$CH_2$—C(O)—NH—, —NH—C(O)—$CH_2$—$CH_2$—C(O)—NH—, —NH—C(O)—$CH_2$—$CH_2$—$CH_2$—C(O)—NH—, —NH—C(O)—$CH_2$—$CH_2$—$CH_2$—$CH_2$—C(O)—NH—, —NH—C(O)—CH=CH—C(O)—NH—, —C(O)—O—$CH_2$—, —$CH_2$—C(O)—O—$CH_2$—, —$CH_2$—$CH_2$—C(O)—O—$CH_2$—, —C(O)—O—$CH_2$—$CH_2$—, —NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$—, —$CH_2$—$CH_2$—NH—C(O)—$CH_2$—$CH_2$—, —C(O)—NH—$CH_2$—, —C(O)—NH—$CH_2$—$CH_2$—, —O—C(O)—NH—$CH_2$—, —O—C(O)—NH—$CH_2$—$CH_2$—, —NH—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—, —$CH_2$—$CH_2$—C(O)—$CH_2$—, —$CH_2$—$CH_2$—C(O)—$CH_2$—$CH_2$—, —$CH_2$—$CH_2$—$CH_2$—C(O)—, —$CH_2$—$CH_2$—$CH_2$—C(O)—NH—$CH_2$—$CH_2$—NH—, —$CH_2$—$CH_2$—$CH_2$—C(O)—NH—$CH_2$—$CH_2$—NH—C(O)—, —$CH_2$—$CH_2$—$CH_2$—C(O)—NH—$CH_2$—$CH_2$—NH—C(O)—$CH_2$—, —$CH_2$—$CH_2$—$CH_2$—C(O)—NH—$CH_2$—$CH_2$—, bivalent cycloalkyl, and amino acids.

Also included as a linker group are: (a) —N($R^6$)—, where $R^6$ is H or an organic radical selected from the group consisting of alkyl, substituted alkyl, alkenyl, substituted alkenyl, alkynyl, substituted alkynyl, aryl and substituted aryl; and —NH—C(O)—O—$(CH_2)_h$—$(OCH_2CH_2)_j$— and —O—C(O)—NH—$(CH_2)_h$—$(OCH_2CH_2)_j$—, where (h) is zero to six, and (j) is zero to 20. Other exemplary spacer moieties have the following structures: —C(O)—NH—$(CH_2)_{1-6}$—NH—C(O)—, —NH—C(O)—NH—$(CH_2)_{1-6}$—NH—C(O)—, and —O—C(O)—NH—$(CH_2)_{1-6}$—NH—C(O)—, wherein the subscript values following each methylene indicate the number of methylenes contained in the structure, e.g., $(CH_2)_{1-6}$ means that the structure can contain 1, 2, 3, 4, 5 or 6 methylenes.

In the Formulae provided herein, a linker group adjacent to "X" may optionally include a carbon atom attached to the "X" (generally oxygen or nitrogen). A linker group can comprise a heteroatom-containing moiety (e.g., NH, O, urethane, urea) and may further contain methylene or other alkylene groups flanking one or both sides. A linker group can be an alkylene chain, optionally containing one or more oxygen or sulfur atoms (i.e., including an ether or thioether linkage). Also included are alkylene chains containing a nitrogen atom (i.e., an amine linkage).

Each linker group within the Formulae provided herein is preferably hydrolytically stable; however, a given linker group may contain a releasable linkage, such as a carboxylate ester, phosphate ester, and orthoester linkage.

Additionally, any linker group within the Formulae provided herein may optionally further include an ethylene oxide oligomer chain comprising 1 to 20 ethylene oxide monomer units (i.e., —$(CH_2CH_2O)_{1-20}$).

In the Formulae provided herein, one or more functional groups (e.g., $G^1$, $G^2$ and $G^3$) may be present. Generally, a functional group (when present) is intended to react with a complementary functional group on another molecule to thereby form the various conjugates and structures provided herein. One of ordinary skill in the art will appreciate which pairs of functional groups (as well as what reactions conditions of solvent, temperature, amount of materials, time, and so forth) are sufficient to allow for complementary functional groups to react and form covalent bonds. The functional group typically comprises an electrophilic or nucleophilic group that provides for covalent attachment with a corresponding nucleophilic or electrophilic group.

Preferred nucleophilic groups include amine, hydroxy, and thiol, particularly amine.

Examples of electrophilic functional groups include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, halosilane, and phosphoramidate. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, etc., as well as hydrates or protected derivatives of any of the above moieties (e.g. aldehyde hydrate, hemiacetal, acetal, ketone hydrate, hemiketal, ketal, thioketal, thioacetal). Another useful conjugation reagent is 2-thiazolidine thione.

The term "carboxylic acid derivative" encompasses various functional groups that include a carbonyl group with an attached heteroatom, such as ester, thioester, anhydride, amide, acid halide, nitrile, carbamate, carbonate, isocyanate, and isothiocyanate. An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters (referred to as active or activated esters) include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g., hydroxy, thio, and amino groups, to produce various bond types. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, will react with hydroxyl or amino groups to form further carbonates or carbamates, respectively. Isocyanates (R—N=C=O) react with hydroxyl or amino groups to form, respectively, carbamate (RNH—C(O)—OR') or urea (RNH—C(O)—NHR') linkages. Phosphoramidites can be reacted with hydroxyl reagents, followed by oxidation, to form phosphate esters (as in conventional oligonucleotide synthesis).

Aldehydes, ketones, glyoxals, diones and their hydrates or alcohol adducts (i.e., aldehyde hydrate, hemiacetal, acetal, ketone hydrate, hemiketal and ketal) are preferably reacted with amines, followed by reduction of the resulting imine, if desired, to give an amine linkage (reductive amination). Alternatively, these groups can be reacted with hydroxyl containing groups, to form further acetals, ketals, and so forth. In this case, the linkages formed are subject to hydrolytic degradation, which may be desirable, as discussed further below.

Several of the electrophilic functional groups include electrophilic double bonds to which nucleophilic groups, such a thiols, can be added, to form, for example, thioether bonds. These groups include maleimides, vinyl sulfones, vinyl pyridine, acrylates, methacrylates and acrylamides. Other groups comprise leaving groups which can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Silanes, including halosilanes and alkoxysilanes, react with hydroxy- or oxide-containing compounds, or surfaces such as glass, to form siloxanes.

Where an imine-containing structure is desired to be provided in reduced form, techniques known to those of ordinary skill in the art can be used. For example, a reducing agent (such as sodium borohydride) can be used to reduce the imine.

As used herein, a "chitosan" is understood to include both chitosan and chitin. Chitin is understood as encompassing linear polysaccharides comprised of 1-4 linked 2-amino-2-deoxy-β-D-glucose (GlcN) and the N-acetylated analogue 2-acetamido-2-deoxy-β-D-glucose (GlcNAc) monomers. It is understood that commercially available forms of chitin may contain deacetylated monomers and that commercially available forms of chitosan may contain acetylated monomers as well; both versions are understood as being encompassed within the term "chitosan." Further, as used herein, the term "chitosan" also includes methylated versions in which one or more of the amino groups are mono-, di- or tri-methylated.

The amine groups in a chitosan have a pKA of about 6.5, thereby generally resulting in a polycationic polymer under neutral conditions. Structurally, exemplary forms of a chitosan for use herein fall within at least one of the following structures:

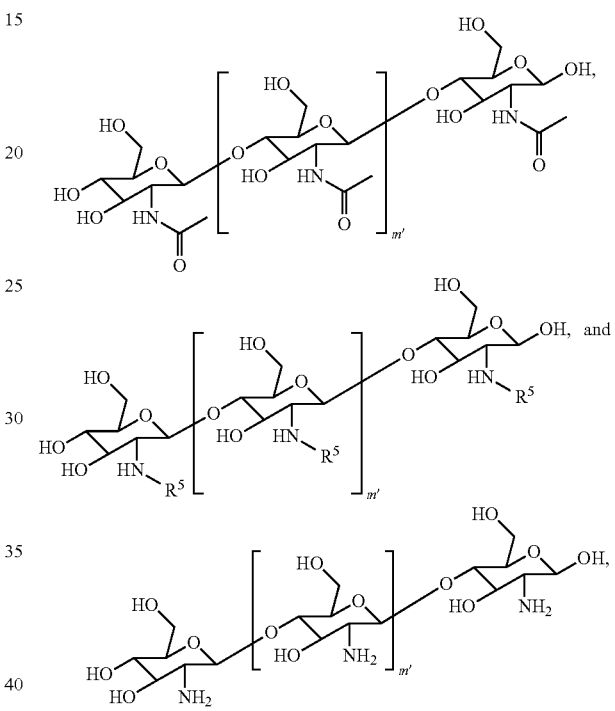

wherein m' is defined to give a molecular weight of the chitosan of from about 500 Daltons to about 1,000,000 Daltons, and R$^5$, in each appearance within the structure, is independently selected from the group consisting of H and —C(O)CH$_3$ (wherein deacetylated versions will have R$^5$ being defined as H relatively more than —C(O)CH$_3$).

Typically, the weight-average molecular weight of the chitosan is from about 500 Daltons to about 300,000 Daltons. Exemplary ranges, however, include weight-average molecular weights in the range of greater than 500 Daltons to about 150,000 Daltons, in the range of from about 600 Daltons to about 125,000 Daltons, in the range of from about 700 Daltons to about 70,000 Daltons, in the range of greater than 800 Daltons to about 50,000 Daltons, in the range of from about 900 Daltons to about 25,000 Daltons, in the range of from about 1,000 Daltons to about 22,000 Daltons, in the range of from about 1,000 Daltons to about 20,000 Daltons, in the range of from about 1,000 Daltons to about 15,000 Daltons, in the range of from about 2,000 Daltons to about 12,000 Daltons, in the range of from about 2,000 Daltons to about 5,000 Daltons, in the range of from about 6,000 Daltons to about 12,000 Daltons, and in the range of from about 2,000 Daltons to about 10,000 Daltons. For any given water-soluble polymer, PEGs having a molecular weight in one or more of these ranges are preferred.

Typically, the percent deacetylation of the raw material chitosan (percent free amine groups) is from about 50% to about 100%. Exemplary ranges, however, include deacetylation percentages in the range of 55% to about 98%, in the range of 65% to about 93%, in the range of 74% to about 90%, and in the range of from about 95% to about 99.9%, and exemplary percentages include: about 50%, about 55%, about 60%, about 65%, about 70%, about 75%, about 80%, about 85%, about 90% about 95%, about 96%, about 97%, about 98%, about 99%, greater than 95%, greater than 96%, greater than 97%, greater than 98% and greater than 99%.

With respect to the water-soluble, non-peptidic polymer, the water-soluble polymer is non-peptidic, nontoxic, non-naturally occurring and biocompatible. With respect to biocompatibility, a substance is considered biocompatible if the beneficial effects associated with use of the substance alone or with another substance (e.g., an active agent such as an siNA) in connection with living tissues (e.g., administration to a patient) outweighs any deleterious effects as evaluated by a clinician, e.g., a physician. With respect to non-immunogenicity, a substance is considered non-immunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the water-soluble, non-peptidic polymer is biocompatible and non-immunogenic.

Further, the polymer is typically characterized as having from 2 to about 300 termini. Examples of such polymers include, but are not limited to, poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly($\alpha$-hydroxy acid), poly(vinyl alcohol), polyphosphazene, polyoxazoline, poly(N-acryloylmorpholine), and combinations of any of the foregoing.

The polymer is not limited to a particular structure and can be linear (e.g., alkoxy PEG or bifunctional PEG); branched or -multi-armed (e.g., forked PEG or PEG attached to a polyol core), dendritic, or with degradable linkages. Moreover, the internal structure of the polymer can be organized in any number of different patterns and can be selected from the group consisting of homopolymer, alternating copolymer, random copolymer, block copolymer, alternating tripolymer, random tripolymer, and block tripolymer.

Typically, activated PEG and other activated water-soluble polymers (i.e., polymeric reagents) are activated with a suitable activating group appropriate for coupling to a desired site on the siNA. Thus, a polymeric reagent will possess a reactive group for reaction with the siNA. Representative polymeric reagents and methods for conjugating these polymers to an active moiety are known in the art and further described in Zalipsky, S., et al., "*Use of Functionalized Poly(Ethylene Glycols) for Modification of Polypeptides*" in Polyethylene Glycol Chemistry: Biotechnical and Biomedical Applications, J. M. Harris, Plenus Press, New York (1992), and in Zalipsky (1995) *Advanced Drug Reviews* 16:157-182.

Typically, the weight-average molecular weight of the water-soluble polymer in the conjugate is from about 100 Daltons to about 150,000 Daltons. Exemplary ranges, however, include weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons. For any given water-soluble polymer, PEGs having a molecular weight in one or more of these ranges are preferred.

Branched versions of the water-soluble polymer (e.g., a branched 40,000 Dalton water-soluble polymer comprised of two 20,000 Dalton polymers) having a total molecular weight of any of the foregoing can also be used.

When used as the polymer, PEGs will typically comprise a number of ($OCH_2CH_2$) monomers [or ($CH_2CH_2O$) monomers, depending on how the PEG is defined]. As used throughout the description, the number of repeating units is identified by the subscript "n" in "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

One particularly preferred polymer is an end-capped polymer, that is, a polymer having at least one terminus capped with a relatively inert group, such as a lower $C_{1-6}$alkoxy group, although a hydroxyl group can also be used. When the polymer is PEG, for example, it is preferred to use a methoxy-PEG (commonly referred to as mPEG), which is a linear form of PEG wherein one terminus of the polymer is a methoxy ($-OCH_3$) group (or $-CH_3$, again depending on how the PEG is defined), while the other terminus is a hydroxyl or other functional group that can be optionally chemically modified.

In one form useful in one or more embodiments of the present invention, free or unbound PEG is a linear polymer terminated at each end with hydroxyl groups:

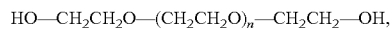

wherein (n) typically ranges from zero to about 4,000.

The above polymer, alpha-, omega-dihydroxylpoly(ethylene glycol), can be represented in brief form as HO-PEG-OH where it is understood that the —PEG-symbol can represent the following structural unit:

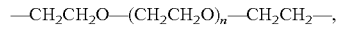

wherein (n) is as defined as above.

Another type of PEG useful in one or more embodiments of the present invention is methoxy-PEG-OH, or mPEG in brief, in which one terminus is the relatively inert methoxy group, while the other terminus is a hydroxyl group. The structure of mPEG is given below:

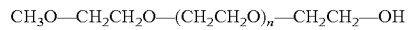

wherein (n) is as described above.

Multi-armed or branched PEG molecules, such as those described in U.S. Pat. No. 5,932,462, can also be used as the PEG polymer. For example, PEG can have the structure:

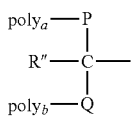

wherein:

$poly_a$ and $poly_b$ are PEG backbones (either the same or different), such as methoxy poly(ethylene glycol);

R" is a nonreactive moiety, such as H, methyl or a PEG backbone; and

P and Q are nonreactive linkages. In a preferred embodiment, the branched PEG polymer is methoxy poly(ethylene glycol) disubstituted lysine. Depending on the specific siNA used, the reactive ester functional group of the disubstituted lysine may be further modified to form a functional group suitable for reaction with the target group within the siNA.

In addition, the PEG can comprise a forked PEG. An example of a forked PEG is represented by the following structure:

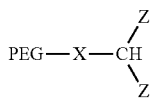

wherein X is a spacer moiety of one or more atoms and each Z is an activated terminal group linked to CH by a chain of atoms of defined length. U.S. Pat. No. 7,223,803 discloses various forked PEG structures capable of use in one or more embodiments of the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, the polymer can also be prepared with one or more weak or releasable linkages in the polymer, including any of the above-described polymers. For example, PEG can be prepared with ester linkages in the polymer that are subject to hydrolysis. As shown below, this hydrolysis results in cleavage of the polymer into fragments of lower molecular weight:

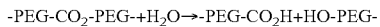

Other hydrolytically releasable linkages, useful as a releasable linkage within a polymer backbone, include: carbonate linkages; phosphate ester linkages formed, for example, by reacting an alcohol with a phosphate group; acetal linkages that are typically formed by reaction between an aldehyde and an alcohol; orthoester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., a phosphoramidite group introduced at the end of a polymer, and a 5' hydroxyl group of an oligonucleotide.

The water-soluble, non-peptidic polymer attached to the chitosan can also be "releasable" (also referred to as "cleavable"). That is, the water-soluble polymer is released (either through hydrolysis, enzymatic processes, or otherwise). In some instances, releasable polymers detach from the chitosan in vivo without leaving any fragment of the water-soluble polymer or linker group on the chitosan. In other instances, releaseable polymers detach from the chitosan in vivo leaving a relatively small fragment (e.g., a succinate tag) on the chitosan. An exemplary releasable polymer includes one that attaches to the chitosan via a carbonate linkage.

Those of ordinary skill in the art will recognize that the foregoing discussion concerning water-soluble, non-peptidic polymers is by no means exhaustive and is merely illustrative, and that all polymeric materials having the qualities described above are contemplated. As used herein, the term "polymeric reagent" generally refers to an entire molecule, which can comprise a water-soluble polymer segment and a functional group.

The conjugates can be formed from reagents bearing multiple polymer "arms" and functional groups, as described in WO10/021,720 and WO10/021,718.

Suitable solvents for carrying out the conjugation reactions described herein include buffers such as aqueous sodium phosphate, sodium acetate, sodium carbonate, phosphate buffered saline (PBS), sodium borate, and N-(2-hydroxyethyl)piperazine-N'-(2-ethanesulfonic acid) (HEPES). Molar excesses of PEG reagent to carbohydrate reagent typically in the range of about 2 to 50, preferably in the range of 2 to 20, and most preferably in the range of 2 to 5. The conjugation reaction is typically carried out at temperatures at or above about room temperature (25° C.), although temperatures may range from about −15° C. to about 100° C., more preferably from about 4° C. to 90° C., more preferably 70° C., for approximately one to 24 hours. Exemplary conjugation reactions are described in Examples 4-5 below.

The exact reaction time is determined by monitoring the progress of the reaction over time. Progress of the reaction is typically monitored by withdrawing aliquots from the reaction mixture at various time points and analyzing the reaction mixture by SDS-PAGE or MALDI-TOF mass spectrometry or any other suitable analytical method.

The strategy for purification of the final conjugate reaction mixture will depend upon a number of factors, such as the molecular weights of the polymers employed. Conjugates having different molecular weights can be isolated using gel filtration chromatography or alternatively based on charge by using ion exchange chromatography. Gel filtration columns suitable for carrying out this type of separation include Superdex® and Sephadex® columns available from Amersham Biosciences. Selection of a particular column will depend upon the desired fractionation range desired. Elution is generally carried out using a non-amine based buffer, such as phosphate, acetate, or the like. The collected fractions may be analyzed by a number of different methods, for example, (i) OD at 280 nm for protein content, (ii) BSA protein analysis, (iii) iodine testing for PEG content, or (iv) by running an SDS PAGE gel, followed by staining with barium iodide.

In one or more embodiments of the invention, a complex is provided, the complex comprising a siRNA complexed with a chitosan, wherein the chitosan is attached to a single water-soluble polymer, preferably a single PEG molecule, as described above.

The water-soluble polymer, following administration, is optionally released from the complex.

The chitosan may be further attached, either directly or through one or more atoms, to a targeting moiety as described below. The composition can also comprise a transfecting agent, e.g., a lipid, phospholipid, anionic and/or cationic lipids, including mixtures of these compositons, including, without limitation, lipids sold under the LIPOFECTAMINE™2000 brand (Life Technologies, Carlsbad Calif.). The transfection agent may be combined with the complex, or it can be covalently attached, either directly or through one or more atoms, to the chitosan or water-soluble polymer component of the complex.

In addition, a method for delivering a complex is provided, the method comprising the step of subcutaneously administering to the patient a composition comprised of a complex comprising a siNA complexed with a chitosan, wherein the chitosan is attached to a single water-soluble, non-peptidic polymer.

The term "siNA," as used herein, refers to a moiety having human siNA activity. The siNA will also have at least one electrophilic group or nucleophilic group suitable for reaction with a polymeric reagent. In addition, the term "siNA" encompasses both the siNA prior to conjugation as well as the siNA residue following conjugation. As will be explained in further detail below, one of ordinary skill in the art can determine whether any given moiety has siNA activity. Further, the term "siNA" includes any nucleic acid molecule capable of mediating RNA interference ("RNAi") or gene silencing. The siNA includes, without limitation, a "short interfering nucleic acid" and includes short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, and post-transcriptional gene silencing RNA (ptgsRNA). For example, the siRNA can be a double-stranded oligonucleotide molecule comprising a sense oligonucleotide and an antisense oligonucleotide, wherein the antisense region comprises complementarity to a target nucleic acid molecule. The siRNA can be a single-stranded hairpin oligonucleotide having self-complementary sense and antisense regions, wherein the antisense region comprises complementarity to a target nucleic acid molecule. As used herein, siRNA molecules need not be limited to those molecules containing only RNA, but further encompasses chemically-modified nucleotides and non-nucleotides. In certain embodiments, the short interfering nucleic acid molecules of the invention lack 2'-hydroxy(2'-OH) containing nucleotides. In certain embodiments, short interfering nucleic acids do not require the presence of nucleotides having a 2'-hydroxy group for mediating RNAi and as such, short interfering nucleic acid molecules of the invention optionally do not contain any ribonucleotides (e.g., nucleotides having a 2'-OH group). The microRNAs can be of an agonist or antagonist and including, for example, antagomirs (as described in Krützfeldt et al. (2005) Nature 438(7068): 685-689). The siNA can be single stranded, double stranded or triple stranded.

siNAs may be of a length of about 7 to 50 nucleotides (each strand of a single stranded, double stranded and triple stranded siNA is independently of from about 7 to 50 nucleotides in length). Many siNAs are known in the art. siNAs, particularly in their single-stranded form and individual strands of a double-stranded or triple stranded siNA, generally have the ability to bind to a target with a $K_D$ of about 0.1 nM to about 100 nM.

siNA may be purchased from a commercial source or may be synthetically produced. For example siRNA can be purchased from Applied Biosystems (Foster City, Calif.) and Thermo Fisher Scientific Inc. (Waltham, Mass.). Those of ordinary skill in the art can prepare synthetic versions of siNA based on the references cited herein and elsewhere in the literature. For further details and a discussion of the synthesis of siRNA molecules in general see, U.S. Patent Application Publication No. 2003/0206887.

In some instances, the siNA comprises a first sequence, for example, the antisense sequence of the siNA construct, complementary to a sequence or portion of sequence comprising a sequence represented by GenBank Accession Nos. shown in Table I of U.S. Patent Application Publication No. 2007/0160980 A1, or other sequence listed in that publication.

Further exemplary siNA is a siNA described in one or more of WO07/121,947, WO07/121,956, WO07/084,684, WO06/069782, WO06/023544, WO05/105152, WO05/000320, WO04/035615, European Patent and/or Application Nos. EP1857547, EP1771206, EP1527176, EP1638580, EP1551868, EP1536827, EP1527176, U.S. Patent Application Publication Nos. 2004/0180351 and 2005/0043263.

Still further exemplary siNA is siNA described in one or more of U.S. Pat. Nos. 5,898,031, 6,107,094, 7,056,704, 7,078,196, European Patent and Application Nos. EP1144623, EP1214945, EP1352061, German Patent 20023125, and U.S. Patent Application Publication Nos. 2005/0176667, 2005/0186591, 2005/0288244, 2006/0008822, 2006/0035254, 2006/0287260, 2007/0054279, 2007/0161595, 2007/0185050, 2007/0197460, 2007/0213292, 2007/0275465 and 2008/0194512.

Still further exemplary siNA is siNA described in one or more of the following U.S. Patent Application Publication Nos. 2005/0244858, 2005/0277610 and 2007/0265220.

Still further exemplary siNA is siNA described in one or more of the following publications Rose et al. (2005) Nucleic Acid Res. 33(13):4140-4156, Kim et al. (2005) Nat. Biotechnol. 23(2):222-226 and Amarzguioui et al. (2006) Nature Protocol 1(2):508-517.

Still further exemplary siNA is siNA described in one or more of the following U.S. Patent Application Publication Nos. 2002/0086356, 2003/0108923, 2007/0229266, 2004/0259247, 2004/0259248, 2005/0026278, 2005/0059005, 2005/0182005, 2005/0227934, 2005/0234006, 2005/0234007, 2006/0166910, 2006/0212950, 2007/0003960, 2007/0003961, 2007/0003962, 2007/0003963, 2007/0093445 and 2007/0287179.

Still further exemplary siNA is siNA described in one or more of the following U.S. Patent Application Publication Nos. 2003/0190654, 2004/0001811, 2004/0038921, 2004/0053875, 2004/0072779, 2004/0091457, 2004/0102408, 2004/0121348, 2004/0126791, 2004/0175703, 2005/0074757, 2005/0100907 and 2008/0070856.

Still further exemplary siNA is siNA described in one or more of the following U.S. Patent Application Publication Nos. 2006/0014289, 2006/0035815, 2006/0122137, 2006/0142230, 2006/0160123, 2007/0155658, 2007/0172430, 2007/0213257, 2007/0213293, 2007/0254362, 2007/0269892, 2007/0275923, 2007/0276134, 2007/0281900, 2007/0293449, 2007/0293657 and 2008/0076701.

In selected embodiments, the complexes of the invention further comprise a targeting moiety. A targeting moiety may comprise an antibody or a fragment of an antibody, a protein or a fragment thereof, a receptor or a subunit thereof, a peptide, a lipid, a carbohydrate, a polymer, a radiolabel, or other suitable targeting moiety. For example, an antibody to a cell surface receptor or the receptor's ligand may be used as a targeting moiety that would deliver the complex to cells expressing the receptor on its surface. Other examples of targeting moieties and their targets include: glucose or mannose-terminal glycoproteins for macrophages; galactose-terminal glycoproteins for hepatocytes; phosphovitellogenins for developing oocyte; fibrin for epithelial cells; and insulin and/or other hormones and transferring for various cell types. Targeting moieties are WO10/021,720 and WO10/021,718.

The complexes of the invention can be prepared by mixing the siNA with the monoconjugated (i.e., monoPEGylated) chitosan, as described above, and other optional components as described herein. By "mixing" is meant a combining or physical mixture of substances, typically followed by the application of energy to the system, such as stirring or agitating. Formation of a complex of the invention is exemplified in Example 5 below.

Complexes of siRNA with a chitosan-polymer monoconjugate, as disclosed herein, are typically part of a composition. Generally, such a composition comprises a plurality of complexes, and each complex may comprise a single type of siNA or two or more different siNA moieties. Optimally, substantially all complexes in the composition (e.g., 85% or more of the plurality of conjugates in the composition) each comprise the same siNA.

The complexes can be purified to obtain/isolate different complex species. The strategy for purification of the final complex reaction mixture will depend upon a number of factors, including, for example, the molecular weight of the components employed, the particular siNA, the desired dosing regimen, and so forth.

If desired, complexes having different molecular weights can be isolated using gel filtration chromatography and/or ion exchange chromatography. That is to say, gel filtration chromatography is used to fractionate differently sized complexes on the basis of their differing molecular weights.

Optionally, the composition of the invention further comprises a transfection agent to enhance, for example, the intracellular update of one or more components of the complex. Exemplary transfection agents include, but are not limited to, DEAE, dextran, DEAE-dextran, calcium phosphate, cationic lipids, and the like.

Optionally, the composition of the invention further comprises a pharmaceutically acceptable excipient. If desired, the pharmaceutically acceptable excipient can be added to a complex to form a composition.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The composition can also include an antimicrobial agent for preventing or deterring microbial growth. Nonlimiting examples of antimicrobial agents suitable for one or more embodiments of the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in one or more embodiments of the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of complex in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The compositions encompass all types of formulations and in particular those that are suited for injection, e.g., powders or lyophilates that can be reconstituted as well as liquids. Examples of suitable diluents for reconstituting solid compositions prior to injection include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned.

In some embodiments of the invention, the compositions comprising the complexes may further be incorporated into a suitable delivery vehicle. Such delivery vehicles may provide controlled and/or continuous release of the complexes and may also serve as a targeting moiety. Non-limiting examples of delivery vehicles include, adjuvants, synthetic adjuvants, microcapsules, microparticles, liposomes, and yeast cell wall particles. Yeast cells walls may be variously processed to selectively remove protein component, glucan, or mannan layers, and are referred to as whole glucan particles (WGP), yeast beta-glucan mannan particles (YGMP), yeast glucan particles (YGP), *Rhodotorula* yeast cell particles (YCP). Yeast cells such as *S. cerevisiae* and *Rhodotorula* sp. are preferred; however, any yeast cell may be used. These yeast cells exhibit different properties in terms of hydrodynamic volume and also differ in the target organ where they may release their contents. The methods of manufacture and characterization of these particles are described in U.S. Pat. Nos. 5,741,495; 4,810,646; 4,992,540; 5,028,703; 5,607,677, and U.S. Patent Applications Nos. 2005/0281781, and 2008/0044438. In one or more embodiments, the delivery vehicle is not a liposomal in nature (i.e., lacks liposomes).

The compositions of one or more embodiments of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

With respect to pulmonary delivery of the complexes described herein, it is preferred to employ one or more of the approaches described in U.S. Pat. Nos. 6,565,885; 6,946,117; 6,309,623; and 6,433,040; the contents of all of which are hereby incorporated herein by reference in their entirety.

The invention also provides a method for administering a complex as provided herein to a patient suffering from a condition that is responsive to treatment with complex. The method comprises administering to a patient, generally via injection, a therapeutically effective amount of the complex (preferably provided as part of a pharmaceutical composition). As previously described, the complexes can be administered injected parenterally by intravenous injection. Advantageously, the complex can be administered by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The method of administering may be used to treat any condition that can be remedied or prevented by administration of the complex. Those of ordinary skill in the art appreciate which conditions a specific complex can effectively treat. Advantageously, the complex can be administered to the patient prior to, simultaneously with, or after administration of another active agent.

The actual dose to be administered will vary depending upon the age, weight, and general condition of the subject as well as the severity of the condition being treated, the judgment of the health care professional, and complex being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day. A given dose can be periodically administered up until, for example, symptoms of organophosphate poisoning lessen and/or are eliminated entirely.

The unit dosage of any given complex (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated herein by reference in their entireties.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains. $^1$H NMR (nuclear magnetic resonance) data was generated by an NMR spectrometer.

Example 1

Preparation of Chitosan (3-5K) tetra(ethylene glycol) maleimidopropionamide

Initially, following the schematic provided immediately below, α-oxyamino-tetra(ethylene glycol)-ω-maleimidopropionamide (1) was prepared ("Step A").

-continued

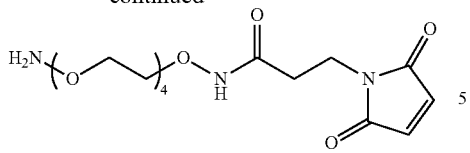

(1)

To a solution of α,ω-bis-oxyaminotetra(ethylene glycol) (2.0 g) and triethylamine (1.0 ml) in acetonitrile (20 ml) was added dropwise a ten-fold excess of 3-maleimidopropionic acid, N-succinimidyl ester (Pierce) while stirring and maintaining the liquid temperature at ~25° C. After stirring for an additional two hours, the solids were filtered off and the solvent was removed by vacuum distillation. The residue was dissolved in methylene chloride and extracted with water. The $CH_2Cl_2$ extract was evaporated and distilled water was added to dissolve the residue. This solution, containing a mixture of the desired product 1 and a large amount of bis-TEG-maleimide, was chromatographed on a POROS cation exchange resin to provide 0.26 g of the desired product 1. This product was used directly in the next step.

Next, following the schematic provided immediately below, chitosan (3-5K) tetra(ethylene glycol) maleimidopropionamide (2) was prepared.

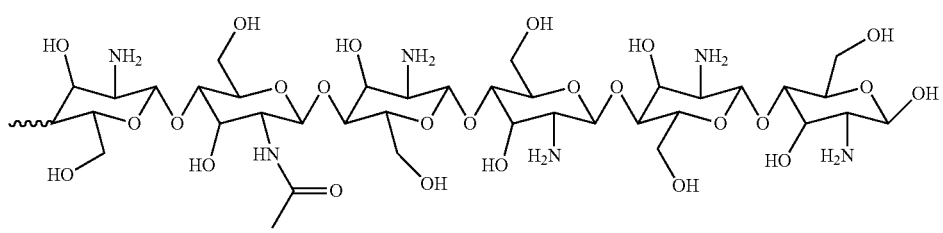

(2)

To a solution of chitosan 3-5K (Kitto Life, Kyongki-Do, Korea, 0.1 g; MW=3000-5000 by GPC) in 0.5M sodium phosphate buffer, pH=5 (2 mL), α-oxyamino-tetra(ethylene glycol)-ω-maleimidopropionamide (1) (prepared in step A above, 0.060 g) was added. Acetonitrile (2 mL) was added slowly to the solution. The mixture was stirred overnight at 70° C., then cooled to room temperature and dialyzed for 3 hours against DI water using Dialysis Cassette MWCO 3500 (Pierce). The water was distilled off under reduced pressure.

The wet product was dried under vacuum overnight giving 0.13 g of 2 as a yellowish solid. NMR analysis performed in D2O showed that the substitution of end groups of chitosan with maleimide substitution was ≥90%.

Example 2

Preparation of Oxyimine-Linked Chitosan (10K) Butanoic Acid (7)

Initially, following the schematice shown below, tetra(ethylene glycol)-α-aminooxyacetamide-ω-butanoic acid (6) was prepared from the tetra(ethylene glycol)-monobutanoic acid, orthoester (3).

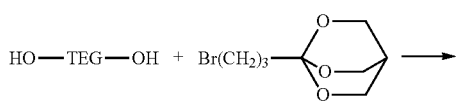

-continued

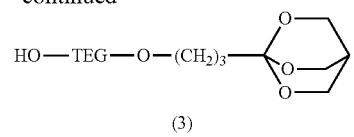

(3)

A solution of tetra(ethylene glycol) (97.1 g, 0.5 mole) in toluene (200 ml) was azeotropically dried by distilling off toluene under reduced pressure. The dried tetra(ethylene glycol) was dissolved in anhydrous toluene (180 ml), and 1.0 M solution of potassium tert-butoxide in tert-butanol (120 ml, 0.12 moles) and 1-(3-bromopropyl)-4-methyl-3,6,7-trioxabicyclo[2,2,2]octane (25.1 g, 0.1 mole) were added. The mixture was placed under an argon atmosphere, heated to 70° C. and stirred overnight. After cooling to room temperature, the mixture was filtered and the solvents were distilled off under reduced pressure. The crude product was dissolved in 1000 ml of deionized water and the disubstituted product was removed by extraction with ethyl acetate (2×100 ml). Sodium chloride (100 g) was added and the product was extracted with dichloromethane (200, 100, and 100 ml). The extract was dried (MgSO$_4$) and the solvent was distilled off under reduced pressure. The crude product (3) (26.6 g) was dissolved in 300 ml of deionized water and extracted with dichloromethane (200, 100, and 50 ml). The extract was dried (MgSO$_4$) and the solvent was distilled off under reduced pressure. Yield: 23.4 g. NMR (d$_6$-DMSO): 0.74 ppm (s, —CH$_3$, orthoester) 1.56 ppm (m, —CH$_2$—CH$_2$-orthoester), 3.51 ppm (bm, —OCH$_2$CH$_2$O—), 3.80 ppm (s, —CH$_2$, orthoester), 4.58 ppm (t, —OH). Purity: ~100%.

Next, following the schematic provided immediately below, tetra(ethylene glycol)-α-mesylate-ω-butanoic acid, orthoester (4) was prepared.

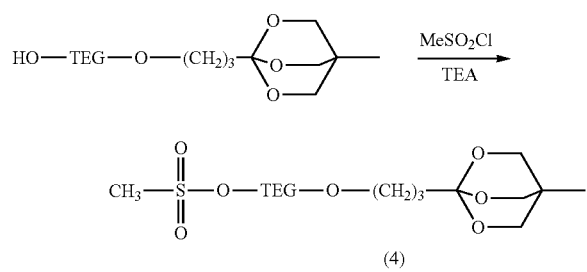

A mixture of tetra(ethylene glycol) monobutanoic acid orthoester (3) (20 g, 0.0549 moles), prepared in step A above, and toluene (200 ml) was azeotropically dried by distilling off toluene under reduced pressure. The dried tetra(ethylene glycol) monobutanoic acid orthoester was dissolved in anhydrous toluene (200 ml). Then, 40 ml of anhydrous dichloromethane and 15.4 ml of triethylamine (0.1105 moles) were added to the solution followed by the dropwise addition of 7.4 g of methanesulfonyl chloride (0.0646 moles) dissolved in dichloromethane (80 ml) while maintaining the solution temperature at 0-5° C. The solution was stirred an additional 2 h at room temperature under argon atmosphere. The resulting mixture was filtered, sodium carbonate (2 g) was added, and the mixture was stirred 1.0 h. Finally the solution was filtered and the solvents distilled off under reduced pressure. Yield: 23.2 g. NMR (d$_6$-DMSO): 0.74 ppm (s, —CH$_3$, orthoester) 1.56 ppm (m, —CH$_2$—CH$_2$-orthoester), 3.18 ppm (s, CH$_3$-methanesulfonate), 3.51 ppm (bm, —OCH$_2$CH$_2$O—), 3.67 ppm (m, —<u>CH$_2$</u>, —CH$_2$-methanesulfonate), 3.80 ppm (s, —CH$_2$, orthoester), 4.31 ppm (m, —CH$_2$— methanesulfonate). Purity: ~100%.

Next, following the schematic provided below, tetra(ethylene glycol)-α-amine-ω-butanoic acid, orthoester (5) was prepared.

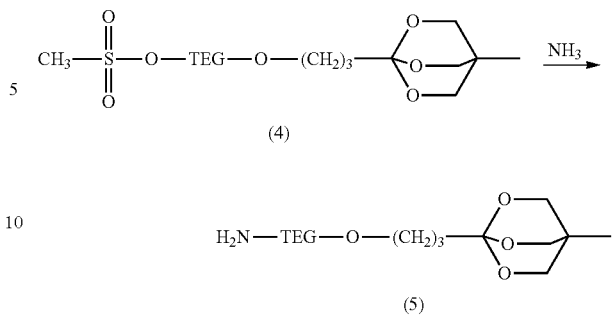

A mixture of tetra(ethylene glycol)-α-mesylate-ω-butanoic acid orthoester (4) (23.2 g), prepared above, ethyl alcohol (100 ml), and concentrated ammonia (1000 ml) was stirred for 88 h at room temperature. The reaction mixture was extracted with dichloromethane (600, 400, and 400 ml), the extract was dried (MgSO$_4$), and the solvent was distilled off under reduced pressure. Yield 19.5 g. NMR (D$_2$O): 0.74 ppm (s, —CH$_3$, orthoester) 1.63 ppm (m, —CH$_2$—CH$_2$-orthoester), 2.71 ppm (t, —CH$_2$-amine), 3.58 ppm (bm, —OCH$_2$CH$_2$O—), 3.67 ppm (m, —<u>CH$_2$</u>—CH$_2$— methanesulfonate), 3.89 ppm (s, —CH$_2$, orthoester). Purity: ~100%.

Thereafter, tetra(ethylene glycol)-α-aminooxyacetamide-ω-butanoic acid (6) was prepared.

To a solution of (Boc-aminooxy)acetic acid (2.0 g, 0.0105 moles; Sigma-Aldrich), N-hydroxysuccinimide (1.20 g, 0.0105 moles), 1-hydroxybenzotriazole (0.30 g, 0.0022 moles) in anhydrous CH$_2$Cl$_2$ (100 ml) cooled to ~5° C., N,N-dicyclohexylcarbodiimide (1.70 g, 0.0115 moles) dissolved in anhydrous CH$_2$Cl$_2$ (30 ml) was added and the mixture was stirred for one hour at 5-15° C. Tetra(ethylene glycol)-α-amine-ω-butanoic acid orthoester (5) (4.0 g, 0.0109 moles), and triethylamine (3.80 ml) were then added, and the mixture was stirred overnight at room temperature under nitrogen atmosphere. The mixture was filtered and the solvent was distilled off. The residue was dissolved in deionized water (80 ml) and the product was extracted with dichloromethane. The extract was dried and the solvent was distilled off under reduced pressure, giving 4.8 of the Boc- and orthoester-protected linker as a liquid product.

The Boc- and orthoester-protected linker, prepared as described above (4.8 g), was dissolved in a mixture of trifluoroacetic acid (30 ml) and anhydrous dichloromethane (30 ml). The resulting solution was stirred for two hours at room temperature, after which time the dichloromethane and trifluoroacetic acid were distilled off under reduced pressure. The residue was dissolved in deionized water (40 ml) and 1.0M sodium hydroxide was added to adjust the pH to 12.2. The mixture was stirred for two hours, keeping the pH 12.1-12.3 by periodical addition of 0.1M sodium hydroxide. The pH was then adjusted to 7.5, and a portion of water was distilled off under reduced pressure, giving 12.2 g of concentrated solution of tetra(ethylene glycol) linker (6) containing oxyamine group and butanoic acid groups.

Next, following the schematic provided immediately below, tetra(ethylene glycol)-α-aminooxyacetamide-ω-butanoic acid (6) was reacted with chitosan.

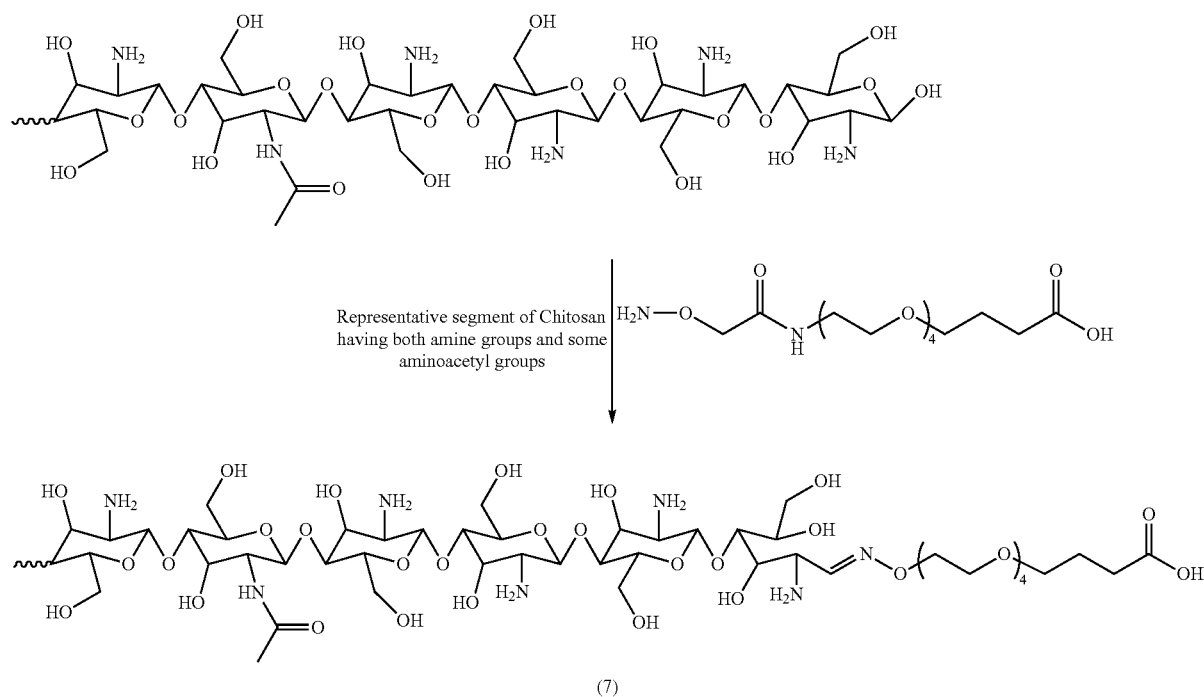

(7)

To a solution of chitosan (10K) (0.2 g, Kitto Life, Kyongki-Do, Korea, containing ~15% acetyl groups, ave. MWN=10000 by GPC) in 0.1M sodium acetate buffer, pH=5.5, a solution of tetra(ethylene glycol)-α-aminooxyacetamide-ω-butanoic acid (6) was added. The pH was readjusted to 5.2 with acetic acid and the mixture was stirred overnight at room temperature. The solution was dialyzed three times against DI water using Dialysis Casette MW CO 10000K (Pierce). The water was distilled off under reduced pressure. The wet product was dried under vacuum overnight giving 2.2 g of (7) as a white solid. NMR analysis performed in $D_2O$ showed that the substitution of end groups of chitosan with butanoic acid groups was ~26%.

Example 3

Preparation of MonoPEGylated (5 KDa) Chitosan (3-5 KDa) (8)

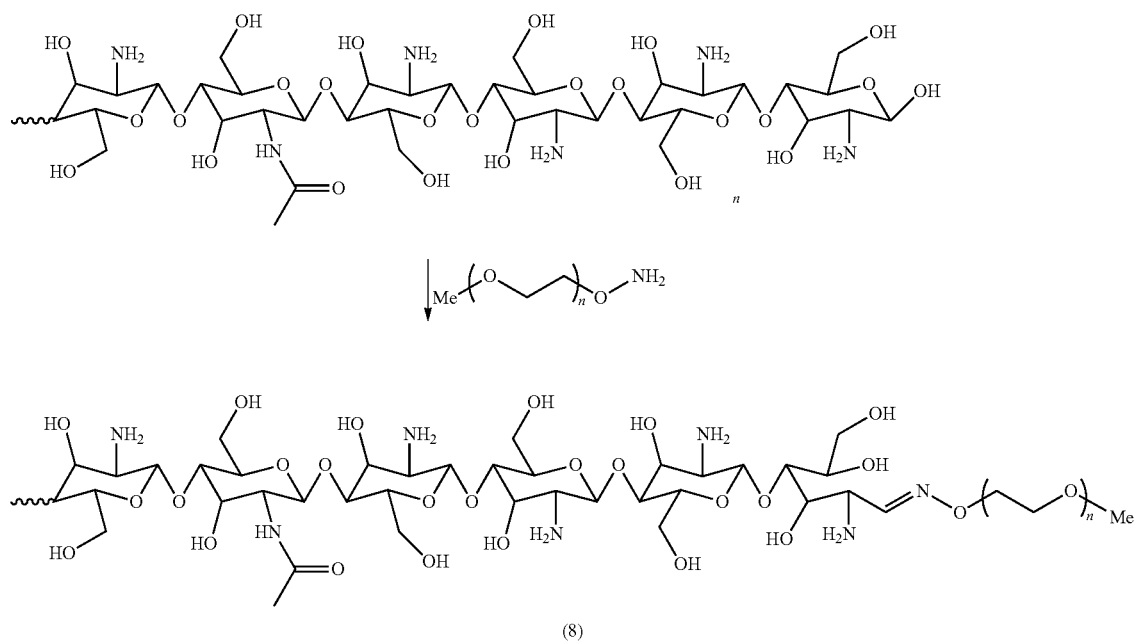

(8)

To a solution of chitosan 3-5K (Kitto Life, Kyongki-Do, Korea, containing ~15% acetyl groups, 0.1 g; MW=3000-5000 by GPC) in 0.5M sodium phosphate buffer, pH=5 (4 mL), mPEG-oxyamine 5K (0.625 g) was added. The mixture was stirred overnight at 70° C. GPC analysis of the product (8) showed that ≥90% of the chitosan was substituted with oxyimino-PEG at the anomeric carbon.

Example 4

Preparation of MonoPEGylated (5K) Chitosan (10K) (9)

To a solution of chitosan 10K (Kitto Life, Kyongki-Do, Korea, containing ~15% acetyl groups, 0.2 g; ave. MW=10000 by GPC) in 0.1M sodium acetate buffer, pH=5 (2 mL), mPEG-oxyamine 5K (0.5 g) was added. Acetonitrile (1 mL) was added slowly, and the mixture was stirred overnight at 70° C. The reaction mixture was cooled to room temperature and adjusted to pH 9 using 1M sodium hydroxide. To the solution was added 2-propanol (25 mL) and chloroform (100 mL). The resulting suspension was transferred to microcentrifuge tubes, and the precipitated product was collected by centrifugation (15 minutes, 13200 rpm). The white suspended layer was removed and dried under vacuum. GPC analysis of the crude product (9) showed approximately 96% of the end groups of chitosan substituted.

Example 5

Preparation of Chitosan (10 KDa) Tetra(ethylene glycol)-ω-Oxyamine

To a solution of 0.1M sodium acetate, pH 5, (2.5 mL), was added chitosan (10 KDa) (500 mg), α,ω-bis-oxyamino-tetra (ethylene glycol) (150 µL), and acetonitrile (1.2 mL) while stirring the reaction mixture at 70° C. After 24 hours, to a stirred solution of acetonitrile (20 mL) was added the reaction mixture and stirring continued for ten minutes. Filter off the precipitated chitosan and dry under vacuum.

Examples 6A, 6B and 6C

Preparation of MonoPEGylated (5 KDa) Chitosan (3-5 KDa)

Example 6A

To a solution of 0.5M sodium chloride, pH 5, (20 mL), was added chitosan (3-5 KDa) (100 mg), mPEG (5 KDa)-oxyamine (675 mg), while the reaction mixture was stirred at room temperature. After seven days the reaction mixture was analyzed by GPC yielding an approximate 30% substitution.

Example 6B

To a solution of 0.5M sodium chloride, pH 5, (20 mL), was added chitosan (3-5 KDa) (100 mg), mPEG (5 KDa)-oxyamine (675 mg), while the reaction mixture was stirred at 70° C. After 24 hours, the reaction mixture was analyzed by GPC yielding an approximate 100% substitution with no identifiable chitosan (3-5 KDa) peak.

Example 6C

To a solution of 0.5M sodium chloride, pH 5, (20 mL), was added chitosan (3-5 KDa) (100 mg), mPEG (5 KDa)-oxyamine (675 mg), while the reaction mixture was stirred at 90° C. After 24 hours, the reaction mixture was analyzed by GPC yielding an approximate 74% substitution.

Example 7

Preparation of Releasable monoPEGylated (20 KDa) Chitosan (10 KDa)

A releasable monoPEGylated conjugate was made using "CAC-FMOC 20K," the preparation of which is described in U.S. Patent Application Publication No. 2006/0293499 and the structure of which is provided below"

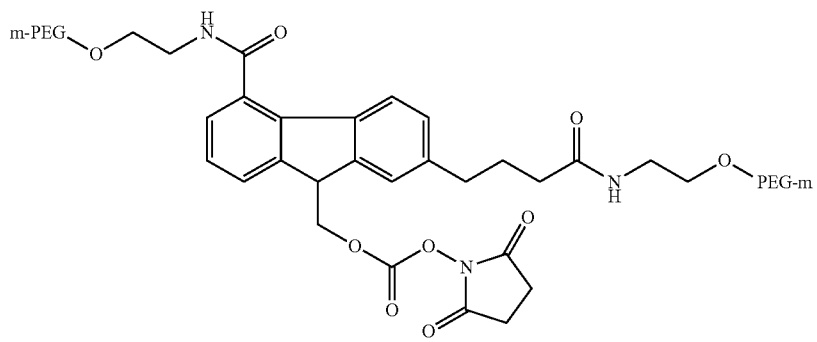

To a solution of 0.1M acetic acid, pH 5, (1 mL) was added chitosan (10 KDa) tetra(ethylene glycol)-ω-oxyamine (90 mg) and the pH of the solution was adjusted to 5 by 1M NaOH. Added CAC-FMOC 20K (360 mg) and stirred the reaction at room temperature for 15 minutes. To the reaction mixture was added 0.1M acetic acid, pH 5, (8 mL) and stirred at room temperature overnight. The product was isolated using POROS 50 cationic exchange and dialyzed using Pierce dialysis cassette MWCO 3500. GPC analysis of the product shows approximately 80% substitution and NMR analysis performed in $D_2O$ shows approximately 86% substituted.

PBS buffer hydrolysis of releasable monoPEGylated (20 KDa) chitosan (10 KDa): To a solution of 25 mM PBS, pH 7.3, (1 mL) was added the monoPEGylated (20 KDa) chitosan (10 KDa) (2 mg). The solution was filtered through a 0.2 µm filter and analyzed for the disappearance of the PEGylated chitosan starting material on an HPLC system with a flow rate of 0.5 mL/min, gradient (A: 0.1M TEAA, B: 80% ACN and 20% 0.1M TEAA) 15% B 0-4 min, 50% B 8 min, and 58.2% B. The column used was a Zorbax 300SB-C3 3.0×150 mm, 3.5 m, column. The calculated half-life was 7.04 hours.

Example 8

Preparation of Targeted MonoPEGylated Chitosan

Use of a targeting agent, such as folate receptor binders (e.g., pemetrexed), is believed to assist accumulation of the complex, if desired, in a tumor. In such a construct, the functional group-bearing water-soluble, non-peptidic polymer within the conjugate of a water-soluble, non-peptidic polymer attached to a chitosan (such as compounds encompassed by Formulae IIIc, IIId, Vc, and Vd) is conjugated to a targeting agent rather than (but in a manner similar to) an siNA. An exemplary construct in this regard, wherein the targeting agent is pemetrexed, is shown below.

PAGE Gel Analysis of monoPEGylated Chitosan Complexed with siRNA by Identifying the Neutralization of the Negatively Charged siRNA and Inhibition of siRNA Migration.

A series of gels were run to compare the stabilities of complexes formed with multiPEGylated chitosan versus monoPEGylated chitosan, across a series of pH values (from 7.3, 6.3 and 5.3) and ratios of PEG-chitosan to siRNA (from 1:1, 2:1, 2.16:1, 5:1, 10:1, 20:1, 50:1)

Preparation of all gels (15% PAGE gel): to a solution of MilliQ purified water (2.5 mL), was added 4× concentrated TAE buffer (2.5 mL), 30% acrylamide/bisacrylamide (5 mL), 10% APS (50 µL), and TEMED (10 µL). The solution was

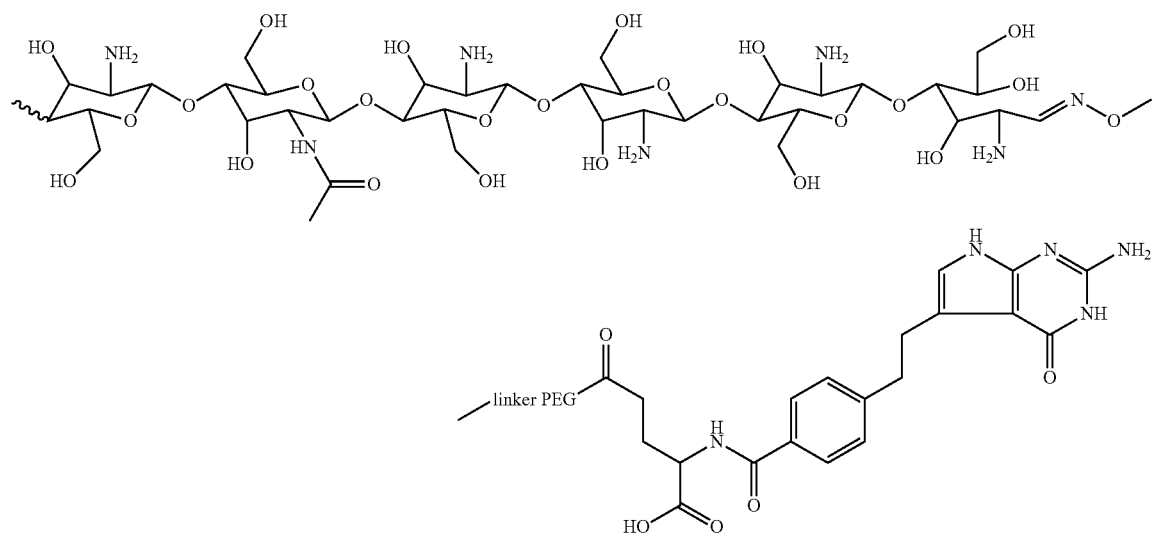

Example 9

Preparation of Ionic Complexes of monoPEGylated-Chitosan (8, 9) with siRNA

The monoPEGylated chitosan conjugates from Examples 3 and 4 (8, 9) were independently dissolved in PBS buffer at pH 5.3, 6.3, or 7.3, with the resulting solution having a final concentration of 5 mg/mL. The siRNA duplex was dissolved in DI water at a final concentration of 2.5 mg/mL. The resulting ionic complexes were prepared by the addition of the specific quantities of the PEGylated chitosan to various quantities of the solution of siRNA. The ratios of PEG-Chitosan to siRNA varied from 5:1 to 50:1. PAGE Gel electrophoresis of siRNA/chitosan ionic complexes confirmed formation of ionic complexes.

Method 1: To a solution of deionized water was added monoPEGylated (5 KDa) chitosan (10 KDa) (5 mg/mL). To a solution of RNase free water was added siRNA (2.5 mg/mL). To a 1.5 mL RNA/DNase free centrifuge vial was added PBS, pH 7.3, monoPEGylated chitosan, and siRNA to achieve the desired ratio.

Method 2: To a solution of deionized water was added monoPEGylated (5 KDa) chitosan (10 KDa) (10 mg/mL). To a solution of RNase free water was added siRNA (2.5 mg/mL). To a 1.5 mL RNA/DNase free centrifuge vial was added PBS, pH 5.3, monoPEGylated chitosan, siRNA, and 0.1M NaOH to achieve the desired ratio at pH 7.3.

vortexed for 30 seconds and transferred into a 10 cm×1 mm cassette and left undisturbed for one hour at room temperature.

Analysis and visualization of all PAGE gels: analysis was performed using TAE buffer at 100 volts for 120 minutes and the gel was visualized using ethidium bromide staining for 15 minutes accompanied by a 30 minute water wash.

Results:

These gels proved stable complexes formed between the monoPEGylated chitosan and the siRNA in comparison to complexes formed between multiPEGylated chitosan, as evidenced by retardation of the siRNA migration on the PAGE gel. This observation is believed to be the result of the chitosan neutralizing the negative charge associated with the siRNA. A neutral complex will not migrate toward the cathode through the gel and thus the siRNA will not be present. As the pH of the solution was decreased, the stability of the complexes formed with monoPEGylated chitosan also increased due to the number of protonated amines present on the chitosan and its ability to complex with the siRNA. Higher ratios of chitosan to siRNA also increased the stability of the complexes, also due to the greater number of protonatable amines present.

The monoPEGylated chitosan consists of an undisrupted linear polymer in which the amine groups are unhindered and freely accessable. Without wishing to be bound by theory, it is believed that these unhindered and freely accessible amine groups afford a more continuous electrostatic interaction with the negative charges located along the siRNA chain leading to formation of stable complexes. In contrast, it is believed that the multiPEGylated chitosan produces a brush or comb-like polymer structure with randomly PEG-substituted amines which disrupt the linearity of the polymer, minimize the number and availability of the amine groups and cause steric hindrance preventing strong complex formation with the siRNA. Therefore, the multiPEGylated chitosan is not able to form very stable complexes with siRNA.

What is claimed is:

1. A conjugate having a single water-soluble, non-peptidic polymer attached to a chitosan, the conjugate encompassed by one of the following two structures;

POLY-$L^1$-X-N=CH-(Chitosan)      (Formula IIIa)

POLY-$L^1$-X-NH—$CH_2$-(Chitosan)      (Formula IIIb)

wherein for each structure:
- POLY is a water-soluble polymer;
- $L^1$ is a linker group;
- X is oxygen or $NR^2$, wherein $R^2$ from the group consisting of hydrogen, methyl, lower alkyl, cycloalkyl, and aryl; and
- Chitosan is a residue of a chitosan.

2. A complex comprising siNA and a plurality of conjugates encompassed by at least one of the structures in claim 1.

* * * * *